United States Patent
Lee

(10) Patent No.: US 7,037,906 B1
(45) Date of Patent: May 2, 2006

(54) METHODS FOR MODULATING TUMOR GROWTH AND METASTASIS

(75) Inventor: Francis Y. Lee, Yardley, PA (US)

(73) Assignees: Oxigene, Inc., Watertown, MA (US); Bristol-Myers Squibb, Inc., Princeton, NJ (US)

( * ) Notice: Subject to any disclaimer, the term of this patent is extended or adjusted under 35 U.S.C. 154(b) by 0 days.

(21) Appl. No.: 10/027,186

(22) Filed: Dec. 20, 2001

Related U.S. Application Data

(60) Provisional application No. 60/258,195, filed on Dec. 22, 2000.

(51) Int. Cl.
 *A61K 31/66* (2006.01)
 *A61K 31/335* (2006.01)
(52) U.S. Cl. .................... 514/130; 514/449
(58) Field of Classification Search ........... 514/130, 514/449
See application file for complete search history.

(56) References Cited

U.S. PATENT DOCUMENTS 5,919,815 A * 7/1999 Bradley et al. ............. 514/449

OTHER PUBLICATIONS

Cahan et al., Cancer Chemotherapy and Pharmacology (1994), 33(5), 441-4 Abstract Only.*

Kerbel Tumor angiogenesis: past, present and the near futture, Carcinogenesis, 2000, vol. 21, No. 3, pp. 505-515.*

* cited by examiner

*Primary Examiner*—Shengjun Wang
(74) *Attorney, Agent, or Firm*—Ivor R. Elrifi; Naomi S. Biswas, Esq.

(57) ABSTRACT

Methods and pharmaceutical compositions for modulating tumor growth or metastasis are provided.

4 Claims, 15 Drawing Sheets

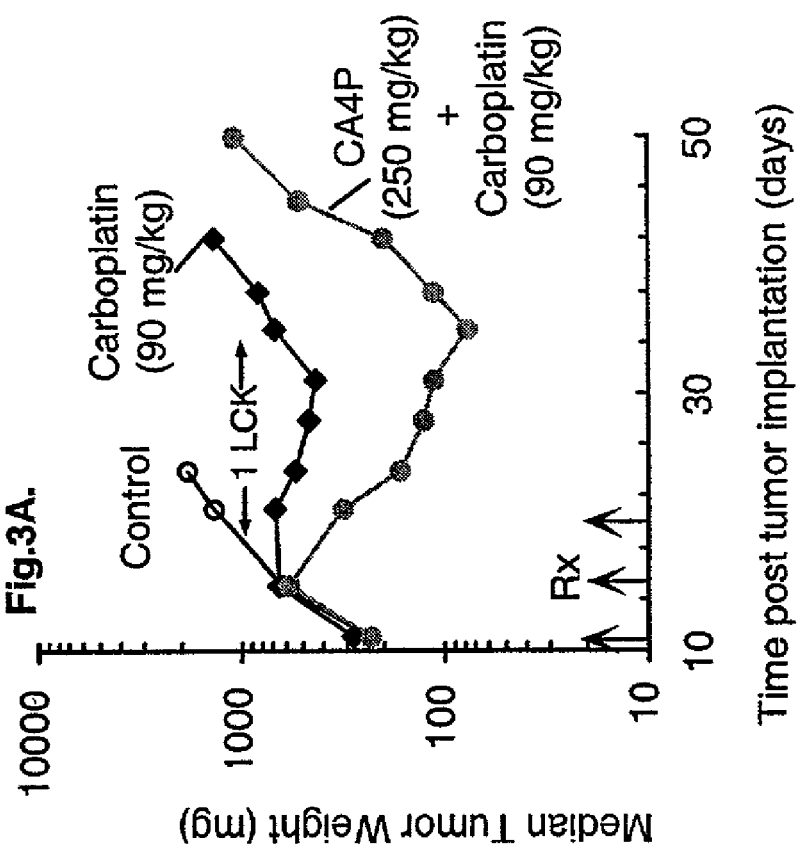
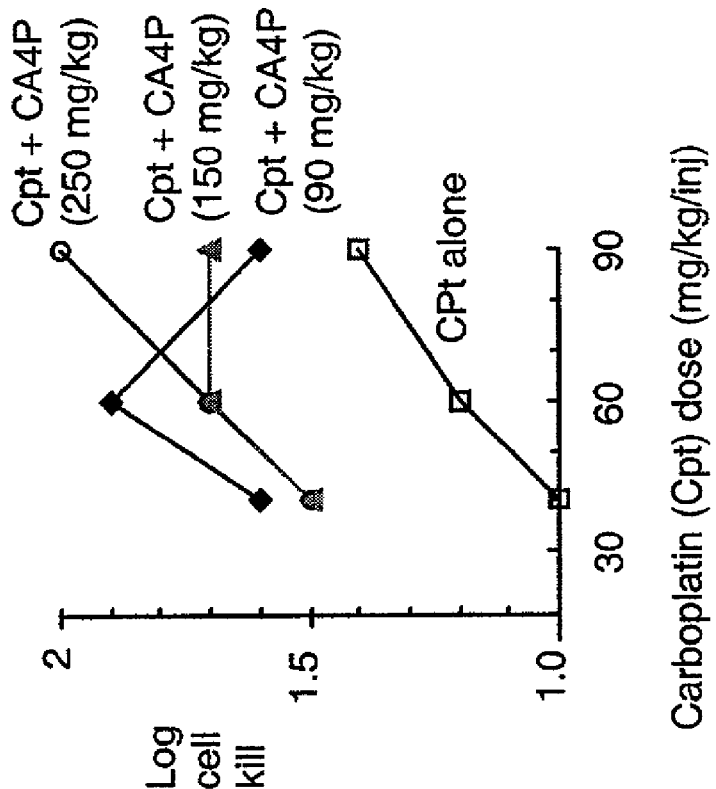
Fig. 3A.
Fig. 3B.

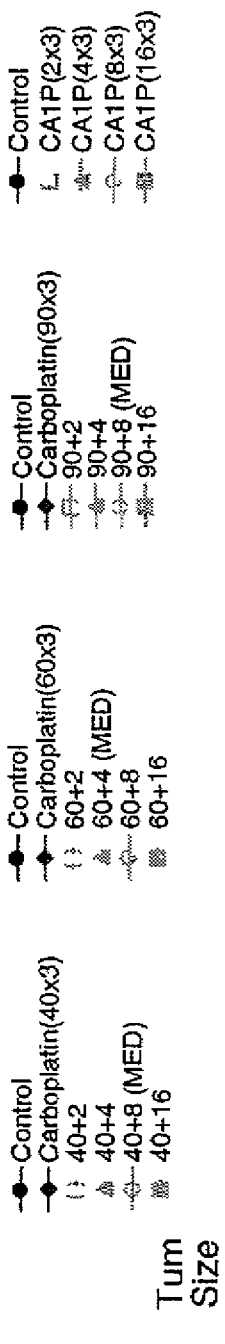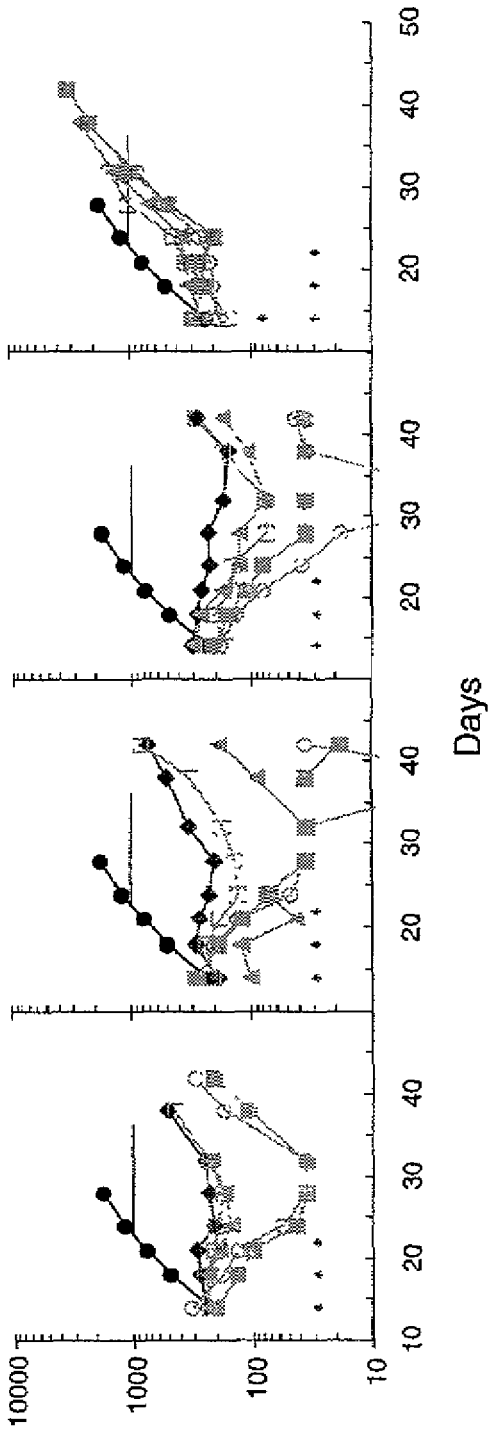
Fig. 13A  Fig. 13B  Fig. 13C  Fig. 13D

METHODS FOR MODULATING TUMOR GROWTH AND METASTASIS This application claims priority to U.S. Provisional Application 60/258,195, filed Dec. 22, 2000, entitled "Methods For Modulating Tumor Growth and Metastasis".

FIELD OF THE INVENTION

This invention relates to the fields of oncology and improved chemotherapy regimens.

BACKGROUND OF THE INVENTION

The disclosure of each literature article and published patent document referred to herein is incorporated by reference herein in its entirety.

Cellular transformation during the development of cancer involves multiple alterations in the normal pattern of cell growth regulation. Primary events in the process of carcinogenesis involve the activation of oncogene function by some means (e.g., amplification, mutation, chromosomal rearrangement), and in many cases, the removal of anti-oncogene function. In the most malignant and untreatable tumors, normal restraints on cell growth are completely lost as transformed cells escape from their primary sites and metastasize to other locations in the body. One reason for the enhanced growth and invasive properties of some tumors may be the acquisition of increasing numbers of mutations in oncogenes, with cumulative effect (Bear et al., Proc. Natl. Acad. Sci. USA 86:7495–7499, (1989)).

Alternatively, insofar as oncogenes function through the normal cellular signaling pathways required for organismal growth and cellular function (reviewed in McCormick, Nature 363:15–16, (1993)), additional alterations in the oncogenic signaling pathways may also contribute to tumor malignancy (Gilks et al., Mol. Cell Biol. 13:1759–1768, (1993)), even though mutations in the signaling pathways alone may not cause cancer.

Several discrete classes of proteins are known to be involved in bringing about the different types of changes in cell division properties and morphology associated with transformation. These changes can be summarized as, first, the promotion of continuous cell cycling (immortalization); second, the loss of responsiveness to growth inhibitory signals and cell apoptotic signals; and third, the morphological restructuring of cells to enhance invasive properties.

The National Cancer Institute has estimated that in the United States alone, 1 in 3 people will be struck with cancer during their lifetime. Moreover approximately 50% to 60% of people contracting cancer will eventually succumb to the disease. The widespread occurrence of this disease underscores the need for improved anticancer regimens for the treatment of malignancy.

Due to the wide variety of cancers presently observed, numerous anticancer agents have been developed to destroy cancer within the body. These compounds are administered to cancer patients with the objective of destroying or otherwise inhibiting the growth of malignant cells while leaving normal, healthy cells undisturbed. Anticancer agents have been classified based upon their mechanism of action. One type of chemotherapeutic is referred to as a metal coordination complex. It is believed this type of chemotherapeutic forms predominantly inter-strand DNA cross links in the nuclei of cells, thereby preventing cellular replication. As a result, tumor growth is initially repressed, and then reversed. Another type of chemotherapeutic is referred to as an alkylating agent. These compounds function by inserting foreign compositions or molecules into the DNA of dividing cancer cells. As a result of these foreign moieties, the normal functions of cancer cells are disrupted and proliferation is prevented. Another type of chemotherapeutic is an antineoplastic agent. This type of agent prevents, kills, or blocks the growth and spread of cancer cells. Still other types of anticancer agents include nonsteroidal aromastase inhibitors, bifunctional alkylating agents, etc.

Unfortunately, deleterious side effects are associated with each of these agents. For example, fluorouracil, a commonly used antineoplastic agent causes swelling or redness of normal skin, black or tarry stools, blood in the urine, chest pain, confusion, diarrhea, shortness of breath, and drowsiness. Administration of fluorouracil has also been associated with fever, chills, cough, sore throat, lower back pain, mouth sores, nausea, vomiting, pain and/or difficulty passing urine. Taxane administration has been associated with cardiovascular events such as syncope, rhythm abnormalities, hypertension and venous thrombosis; bone marrow suppression; neutropenia; anemia; peripheral neuropathy arthralgia/myalgia; nausea/vomiting and alopecia, to name only a few.

Combretastatins are another class of anticancer agents. Combretastatins have been isolated from stem wood of the African tree combretum caffrum (Combretaceae), and are potent inhibitors of microtubulin assembly. Combretastatin A-4 (CA-4) is significantly active against the US National Cancer Institute's (NCI) murine L1210 and P338 lymphocytic leukemia cell lines. In addition, CA-4 was found to compete with combretastatin A-1 (CA-1), another compound isolated from Combretum caffrum, as a potent inhibitor of colchicine binding to tubulin. CA-4 also strongly retards the growth of certain cell lines (ED50<0.01 (g/ml), and is a powerful anti-mitotic agent. See U.S. Pat. No. 4,996,237. Furthermore, an "anti-vascular" mechanism of action for both CA-4 and CA-1 has recently been discovered. Since the solubility of the combretastatins is very limited, prodrugs have been developed, such as combretastatin A-4 phosphate disodium salt and combretastatin A-1 phosphate disodium salt (hereinafter "CA4P" and "CA1P" respectively), to increase the solubility, and thus the efficacy of CA-4 and CA-1. In particular, a number of studies have shown that administration of combretastatin A-4 disodium salt or combretastatin A-1 phosphate disodium salt causes an extensive shut-down of blood flow to the tumor vasculature, leading to secondary tumor cell death. Toxic side effects of CA-4 have also been reported.

There is thus a need in the art to provide superior effective anticancer therapies which minimize patient exposure and the unwanted side effects associated with such agents.

SUMMARY OF THE INVENTION

The present invention provides effective therapeutic methods for modulating tumor growth or metastasis wherein a combination of agents is employed. The methods of the present invention provide advantages such as greater overall efficacy, for example, in achieving synergy or avoiding antagonism, and allow, where desired, a reduction in the amount of one or more of the individual agents employed with a concomitant reduction in side effects. Further, where the tumor to be treated is not optimally responsive to a given anticancer agent, use of the present combination therapy methods can nonetheless provide effective treatment.

In particular, the present invention provides a method for modulating tumor growth or metastasis in an animal, especially a human, in need thereof, comprising sequential or simultaneous administration of a combretastatin A-4 compound or combretastatin A-1 compound and at least one other anticancer agent, in amounts effective therefor. Preferred such agents are described further below. The method of the present invention can provide the aforementioned advantages.

Further, the present inventors have found that certain sequences of administering the combretastatin A-4 compound or combretastatin A-1 compound and the other anticancer agent can, in vivo, potentiate the overall efficacy of the combination. Combretastatin A-4 compounds or combretastatin A-1 compounds, as antivascular agents, modulate blood flow to tumor tissue. By timing the administration of the combretastatin A-4 compound or combretastatin A-1 compound to modulate the flow of blood to the tumor to provide a time-dependent effective tumor concentration of the other anticancer agent, the overall efficacy of the combination is potentiated.

Without wishing to be bound by any molecular theory of action, certain anticancer agents are most efficacious at relatively high tumor concentrations, but are rapidly cleared from tumor tissue. For such agents, the present inventors have found that simultaneous administration of the combretastatin A-4 compound or combretastatin A-1 compound and the other anticancer agent potentiates the effect of the combination. Simultaneous administration allows the other anticancer agent to rapidly accumulate to a peak concentration in tumor tissue, yet "traps" the agent as the vasulature clearing tumor tissue is disrupted by the combretastatin A-4 compound or combretastatin A-1 compound. Such agents are termed herein "Peak Tumor Concentration Agents". Peak Tumor Concentration Agents are thus preferably administered simultaneously with, or within close temporal proximity to, the combretastatin A-4 compound or combretastatin A-1 compound.

Other agents, for example, need not be present at high concentrations, but are effective during a relatively short period of the overall cell cycle. As such agents can become protein-bound and inactive over time when remaining in contact with tumor tissue, they are therefore most efficacious under conditions where a continuing supply of the agent reaches the tumor. Potentiation of the efficacy of combination therapy in these cases can be obtained by administering the anticancer agent and combretastatin A-4 compound or combretastatin A-1 compound sequentially, with sufficient delay between administrations to allow the action of one of the agents before the other. Thus, when such anticancer agent is administered first, followed by a delay before administering the combretastatin A-4 compound or combretastatin A-1 compound, the anticancer agent reaches the tumor tissue over a sufficient duration to allow action of the compound, with subsequent administration of the combretatatin A-4 compound or combretastatin A-1 compound further damaging tumor tissue.

When the combretastatin A-4 compound or combretastatin A-1 compound is administered first, followed by a delay to allow blood flow to the tumor to resume before administering the anticancer agent, the tumor is initially weakened by the combretastatin A-4 compound or combretastatin A-1 compound, followed by further damage to the tumor by the anticancer agent. In this latter case, duration of anticancer agent tumor concentration is more significant than peak concentration. The damage to tumor vasculature by the initial administration of the combretastatin A-4 compound or combretastatin A-1 compound does not prevent the relatively low concentration of anticancer agent needed from reaching the tumor tissue once blood flow resumes. Such agents are termed herein "Duration Exposure Agents". Duration Exposure Agents and the combretastatin A-4 compound or combretastatin A-1 compound are thus preferably administered sequentially, with either administration of the combretastatin A-4 compound or combretastatin A-1 compound first, followed by the anticancer agent, or vice versa, provided that a sufficient delay is allowed between administrations to potentiate the combination. Administration of the anticancer agent after the administration of combretastatin A-4 compound or combretastatin A-1 compound is most preferred for Duration Exposure Agents.

In yet an additional embodiment of the methods of the invention, certain agents are most efficacious when present at relatively high concentrations in tumor tissue over a longer duration (i.e., maximizing the "area under the curve" (AUC) of a plot of concentration over time). Administering such agents first, followed by a delay before administering the combretastatin A-4 compound or combretastatin A-1 compound, allows action of the anticancer agent, with subsequent administration of the combretastatin A-4 compound or combretastatin A-1 compound further weakening the tumor tissue. For such agents, administration of the anticancer agent first avoids premature damage to tumor vasculature and allows sufficient concentrations of anticancer agent to reach the tumor. Such agents are termed herein "High AUC Agents". High AUC Agents and the combretastatin A-4 compound or combretastatin A-1 compound are thus preferably administered sequentially, with administration of the High AUC Agent preceding administration of the combretastatin A-4 compound or combretastatin A-1 compound, provided that a sufficent delay is allowed between administrations to potentatiate the combination.

The present invention therefore provides as a further embodiment, a method for modulating tumor growth or metastasis in an animal in need thereof, especially a human, comprising administration of a combretastatin A-4 compound or combretastatin A-1 compound and at least one anticancer agent, in amounts effective therefor, wherein said combretastatin A-4 compound or combretastatin A-1 compound is administered at a time relative to administration of said anticancer agent sufficient to modulate blood flow to said tumor to provide a time-dependent effective tumor concentration of said anticancer agent. The method of the present invention allows potentiation of the overall efficacy of the combination employed.

The term "time-dependent effective tumor concentration," as used herein, denotes a concentration of the other anticancer agent in the tumor tissue over time (i.e, from administration until the agent is cleared from the body) which potentiates the action of the combination of the combretastatin A-4 compound or combretastatin A-1 compound and other anticancer agent. Thus, where the combination is otherwise antagonistic, "potentiation" can denote use of a combination without antagonistic results. "Potentiation" can also denote achieving an unexpected improvement in the overall efficacy of the combination, such as synergy.

Where simultaneous administration of the combretastatin A-4 compound or combretastatin A-1 compound and at least one anticancer agent is contemplated, the present invention also provides pharmaceutical compositions comprising at least one anticancer agent and a combretastatin A-4 compound or combretastatin A-1 compound. For example, in one aspect, the anticancer agent and/or combretastatin A-4 compound or combretastatin A-1 compound can be present in a subtherapeutic dose for the individual agent, the agents being effective in combination, providing reduced side effects while maintaining efficacy. Alternatively, each agent can be provided at higher doses for the individual agent, such as those found in the Physician's Desk References.

Where simultaneous or sequential administration of the combretastatin A-4 compound or combretastatin A-1 compound and anticancer agent is contemplated, the present invention further provides pharmaceutical kits. Exemplary kits of the invention comprise a first pharmaceutical composition comprising at least one anticancer agent and a second pharmaceutical composition comprising a combretastatin A-4 compound or combretastatin A-1 compound together in a package. The anticancer agent and/or combretastatin A4 compound or combretastatin A-1 compound can be present, for example, in a subtherapeutic dose for the individual agent, the agents being effective in combination and providing reduced side effects while maintaining efficacy. Alternatively, each agent can be provided at a higher dose, such as those found for the agent in the Physician's Desk Reference.

The following definitions are provided to facilitate an understanding of the present invention. As used herein, the term "combretastatin A-4 compound" denotes at least one of combretastatin A-4, prodrugs (preferably phosphate prodrugs) and derivatives thereof, and salts of these compounds. Such compounds include without limitation, combretastatin A-4, and various prodrugs of combretastatin A-4 exemplified by combretastatin A-4 phosphate and salts thereof, especially combretastatin A-4 phosphate disodium salt. Preferred combretastatin A-4 compounds contemplated for use in the methods of the invention are described in WO 00/48606; WO 99/35150; U.S. Pat. No. 5,561,122; U.S. Pat. No. 4,996,237; U.S. Provisional Application Ser. No. 60/232,568, filed Sep. 14, 2000 by John J. Venit, entitled "Combretastatin A-4 phosphate Mono- and Di-Amino Acid Salt Prodrugs" disclosing compounds of the formula I:

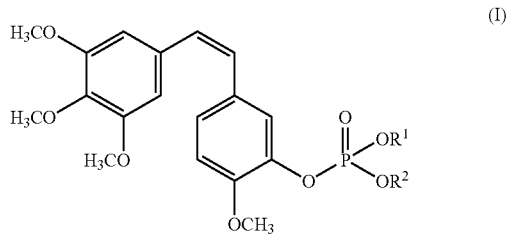

wherein one of $OR^1$ and $OR^2$ is —$O^-$ $QH^+$, and the other is hydroxyl or —$O^-$ $QH^+$, and Q is an amino acid containing at least two nitrogen atoms where one of the nitrogen atoms, together with a proton, forms a quaternary ammonium cation QH+, preferably, where one of $OR^1$ and $OR^2$ is hydroxyl, and the other is —$O^{6-}$ $QH^+$ where Q is L-histidine; and U.S. Provisional Application Ser. No. 60/251,921, filed Dec. 7, 2000 by Mandar V. Dali et al., entitled "Combretastatin A-4 Phosphate Prodrug Mono- and Di-Organic Amine Salts" disclosing compounds having the structure shown in formula I above, wherein one of $OR^1$ and $OR^2$ is —$O^-QH^+$, and the other is hydroxyl or —$O^-QH^+$; and Q is an organic amine containing at least one nitrogen atom which, together with a proton, forms a quaternary ammonium cation, QH+, preferably, where one of $OR^1$ and $OR^2$ is hydroxyl and the other is —$O^-QH^+$ and Q is tris(hydroxymethyl)amino methane ("TRIS"). As mentioned above, each of these documents is incorporated herein by reference in its entirety.

As used herein, the term combretastatin A-1 compound denotes as least one of combretastatin A-1, prodrugs (preferably phosphate prodrugs) and derivatives thereof, and salts of these compounds. Combretastatin A-1 is described in U.S. Pat. No. 5,409,953 to Pettit et al. and has the following general structure:

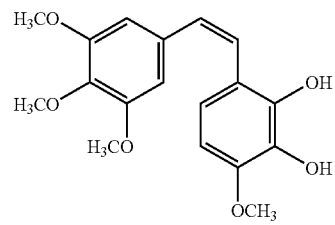

As used herein, the terms "modulate", "modulating" or "modulation" refer to changing the rate at which a particular process occurs, inhibiting a particular process, reversing a particular process, and/or preventing the initiation of a particular process. Accordingly, if the particular process is tumor growth or metastasis, the term "modulation" includes, without limitation, decreasing the rate at which tumor growth and/or metastasis occurs; inhibiting tumor growth and/or metastasis; reversing tumor growth and/or metastasis (including tumor shrinkage and/or eradication) and/or preventing tumor growth and/or metastasis.

The term "anticancer agent" as used herein denotes a chemical compound or electromagnetic radiation (especially, X-rays) which is capable of modulating tumor growth or metastasis. When referring to use of such an agent with a combretastatin A-4 compound or combretastatin A-1 compound, the term refers to an agent other than a combretastatin A-4 compound or combretastatin A-1 compound. Unless otherwise indicated, this term can include one, or more than one, such agents. Thus, the term "anticancer agent" encompasses the use of one or more chemical compounds and/or electromagnetic radiation in the present methods and compositions. Where more than one anticancer agent is employed, the relative time for administration of the combretastatin A-4 compound or combretastatin A-1 compound can, as desired, be selected to provide a time-dependent effective tumor concentration of one, or more than one, of the anticancer agents.

As explained above, numerous types of anticancer agents are exemplary of those having applications in a composition or method of the present invention. Such classes of anticancer agents, and their preferred mechanisms of action, are described below:

1. Alkylating agent: a compound that donates an alkyl group to nucleotides. Alkylated DNA is unable to replicate itself and cell proliferation is stopped. Examples of such compounds include, but are not limited to, busulfan, coordination metal complexes (such as carboplatin, oxaliplatin, and cisplatin), cyclophosphamide (cytoxan), dacarbazine, ifosfamide, mechlorethamine (mustargen), and melphalan;

2. Bifunctional alkylating agent: a compound having two labile methanesulfonate groups that are attached to opposite ends of a four carbon alkyl chain. The methanesulfonate groups interact with, and cause damage to DNA in cancer cells, preventing their replication. Examples of such compounds include, without limitation, chlorambucil and melphalan;

3. Non-steroidal aromatase inhibitor: a compound that inhibits the enzyme aromatase, which is involved in estrogen production. Thus, blockage of aromatase results in the prevention of the production of estrogen. Examples of such compounds include anastrozole and exemstane;
4. Immunotherapeutic agent: an antibody or antibody fragment which targets cancer cells that produce proteins associated with malignancy. Exemplary immunotherapeutic agents include Herceptin which targets HER2 or HER2/neu, which occurs in high numbers in about 25 percent to 30 percent of breast cancers; and anti-CD20 which triggers apoptosis in B cell lymphomas. Additional immunotherapeutic agents include immunotoxins, wherein toxin molecules such as ricin, diphtheria toxin and pseudomonas toxins are conjugated to antibodies which recognize tumor specific antigens. Conjugation can be achieved biochemically or via recombinant DNA methods.
5. Nitrosurea compound: inhibits enzymes that are needed for DNA repair. These agents are able to travel to the brain so they are used to treat brain tumors, as well as non-Hodgkin's lymphomas, multiple myeloma, and malignant melanoma. Examples of nitrosureas include carmustine and lomustine;
6. Antimetabolite: a class of drugs that interfere with DNA and ribonucleic acid (RNA) elongation. These agents are phase specific (S phase) and are used to treat chronic leukemias as well as tumors of breast, ovary and the gastrointestinal tract. Examples of antimetabolites include 5-fluorouracil, methotrexate, gemcitabine (GEMZAR), cytarabine (Ara-C), and fludarabine.
7. Antitumor antibiotic: a compound having antimicrobial and cytotoxic activity. Such compounds also may interfere with DNA by chemically inhibiting enzymes and mitosis or altering cellular membranes. Examples include, but certainly are not limited to bleomycin, dactinomycin, daunorubicin, doxorubicin (Adriamycin), and idarubicin;
8. Mitotic inhibitor: a compound that can inhibit mitosis (e.g., tubulin binding compounds) or inhibit enzymes that prevent protein synthesis needed for reproduction of the cell. Examples of mitotic inhibitors include taxanes such as paclitaxel and docetaxel, epothilones, etoposide, vinblastine, vincristine, and vinorelbine;
9. Radiation therapy: includes but is not limited to X-rays or gamma rays which are delivered from either an externally supplied source such as a beam or by implantation of small radioactive sources.
10. Topoisomerase I inhibitors: agents which interfere with topoisomerase activity thereby inhibiting DNA replication. Such agents include, without limitation, CPT-11 and topotecan.
11. Hormonal therapy: includes, but is not limited to anti-estrogens, such as Tamoxifen, GnRH agonists, such as Lupron, and Progestin agents, such as Megace.

Naturally, other types of anticancer agents that function via a large variety of mechanisms have application in the pharmaceutical compositions and methods of the present invention. Additional such agents include for example, leuocovorin, kinase inhibitors, such as Iressa and Flavopiridol, analogues of conventional chemotherapeutic agents such as taxane analogs and epothilone analogues, antiangiogenics such as matrix metalloproteinase inhibitors, and other VEGF inhibitors, such as ZD6474 and SU6668. Retinoids such as Targretin can also be employed in the pharmaceutical compositions and methods of the invention. Signal transduction inhibitors which interfere with farnesyl transferase activity and chemotherapy resistance modulators, e.g., Valspodar can also be employed. Monoclonal antibodies such as C225 and anti-VEGEr antibodies can also be employed.

As used herein, the phrase "effective amount" of a compound or pharmaceutical composition refers to an amount sufficient to modulate tumor growth or metastasis in an animal, especially a human, including without limitation decreasing tumor growth or size or preventing formation of tumor growth in an animal lacking any tumor formation prior to administration, i.e., prophylactic administration.

As used herein, the term "prodrug"f refers to a precursor form of the drug which is metabolically converted in vivo to produce the active drug. Thus, for example, combretastatin A-4 phosphate prodrug salts or combretastatin A-1 phosphate prodrug salts administered to an animal in accordance with the present invention undergo metabolic activation and regenerate combretastatin A-4 or combretastatin A-1 in vivo, e.g., following dissociation and exposure to endogenous nonspecific phosphatases in the body.

As explained above, the present invention is directed towards a pharmaceutical composition that modulates growth or metastasis of tumors, particularly solid tumors, using a pharmaceutical composition of the present invention, along with methods of modulating tumor growth or metastasis, for example, with a pharmaceutical composition of the present invention.

As used herein, the terms "tumor", "tumor growth" or "tumor tissue" can be used interchangeably, and refer to an abnormal growth of tissue resulting from uncontrolled progressive multiplication of cells and serving no physiological function. A solid tumor can be malignant, e.g. tending to metastasize and being life threatening, or benign. Examples of solid tumors that can be treated or prevented according to a method of the present invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, gastic cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, liver metastases, bile duct carcinoma, choriocarcinoma, seminoma, embryonal carcinoma, thyroid carcinoma such as anaplastic thyroid cancer, Wilms' tumor, cervical cancer, testicular tumor, lung carcinoma such as small cell lung carcinoma and non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Moreover, tumors comprising dysproliferative changes (such as metaplasias and dysplasias) can be treated or prevented with a pharmaceutical composition or method of the present invention in epithelial tissues such as those in the cervix, esophagus, and lung. Thus, the present invention provides for treatment of conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W. B. Saunders Co., Philadelphia, pp. 68 to 79). Hyperplasia is a form of controlled cell proliferation involving an increase in cell number in a tissue or organ, without significant alteration in structure or function. For example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. For a review of such disorders, see Fishman et al., 1985, Medicine, 2d Ed., J. B. Lippincott Co., Philadelphia.

Other examples of tumors that are benign and can be treated or prevented in accordance with a method of the present invention include arteriovenous (AV) malformations, particularly in intracranial sites and myoleomas.

The phrase "Peak Tumor Concentration Agents" refers to anticancer agents which are most efficacious at high tumor concentrations yet are rapidly cleared from the tumor tissue. Such agents are preferably administered simultaneously with or in close temporal proximity to (e.g., as is clinically feasible, especially within one hour of) the administration of the combretastatin A-4 compound or combretastatin A-1 compound in accordance with the invention. Exemplary Peak tumor Concentration Agents include, without limitation, alklating agents such as cytoxan and mitomycin C and metal coordination complexes such as cisplatin, oxaliplatin and carboplatin.

The phrase "Duration Exposure Agents" as used herein refers to agents which can be effective at relatively low tumor concentrations yet which require certain tumor tissue exposure times to be most effective. Such agents are preferably administered sequentially in any order with a combretastatin A-4 compound or combretastatin A-1 compound in accordance with the invention, provided that a sufficient delay is allowed between administrations to potentiate the combination. In a preferred embodiment of the method of the invention, the Duration Exposure Agent is administered after the administration of the combretastatin A-4 compound or combretastatin A-1 compound. Exemplary Duration Exposure Agents include, without limitation, taxanes such as paclitaxel and docetaxel, etoposide, etoposide phosphate, immunotoxins, and epothilones.

The phrase "High AUC Agents" as used herein refers to those agents which show greatest efficacy when present at high concentrations in tumor tissue for extended time periods. Such agents are preferably administered sequentially with a combretastatin A-4 compound or combretastatin A-1 compound in accordance with the invention, wherein the High AUC Agent is administered first, followed by the combretastatin A-4 compound or combretastatin A-1 compound, provided that a sufficient delay is allowed between administrations to potentiate the combination. Exemplary High AUC Agents include, without limitation, adriamycin, CPT-11 (irinotecan), and topotecan.

In one preferred embodiment, Peak Tumor Concentration Agents, such as platinum based anticancer agents, including cisplatin or carboplatin are administered essentially simultaneously with a combretastatin A-4 compound or combretastatin A-1 compound, such as combretastatin A-4 phosphate disodium salt or combretastatin A-1 phosphate disodium salt.

In yet another preferred embodiment, Duration Exposure Agents, including immunotoxins, and taxanes, such as paclitaxel and docetaxel are administered after the combretastatin A-4 compound or combretastatin A-1 compound. Administration of a combretastatin A-4 compound or combretastatin A-1 compound prior to the Duration Exposure Agent extends the exposure time of the tumor tissue to the Duration Exposure Agent.

In an additional preferred embodiment, High AUC Agents such as CPT-11, are administered prior to the administration of the combretastatin A-4 compound or combretastatin A-1 compound (e.g., combretastatin A-4 phosphate disodium salt or combretastatin A-1 phosphate disodium salt). Such agents can preferably be administered, for example, within 24 hours of the administration of the combretastatin A-4 compound or combretastatin A-1 compound, such as within 2–24 hours prior, 3–24 hours prior, 6–24 hours prior, 8–24 hours prior, or 12 to 24 hours prior to administration.

Surprisingly, combinations such as those described above potentiate the efficacy of the combination and can provide the advantages described above. For example, the present methods permit the clinician to administer a combretastatin A-4 compound or combretastatin A-1 compound, such as the phosphate disodium salts of these compounds, and/or anticancer agent, at dosages which are significantly lower than those employed for the single agent. Preferred dosages suitable for administration of the anticancer and combretastatin A-4 compounds or combretastatin A-1 compounds in accordance with the invention are set forth hereinbelow.

Whether administered simultaneously or sequentially, the combretastatin A-4 compound or combretastatin A-1 compound and the at least one anticancer agent can be administered in any amount or by any route of administration effective for the modulation of tumor growth or metastasis, especially treatment of cancer as described herein. The expression "chemotherapeutically effective amount"f, as used herein, refers to a sufficient amount of the compounds of the invention to provide the desired anticancer effect. The exact amount required will vary from subject to subject, the mode of administration of the chemotherapeutic compounds and the like.

The present invention further provides chemotherapeutic pharmaceutical compositions comprising both a combretastatin A-4 compound or combretastatin A-1 compound, and at least one selected anticancer agent and the use thereof in the present methods. Alternatively, the method of the present invention can be carried out using chemotherapeutic pharmaceutical compositions which comprise one of the above-described compounds as the active ingredient, in combination with a pharmaceutically acceptable carrier medium or an auxiliary agent. Thus, in such an embodiment, the combretastatin A-4 compound or combretastatin A-1 compound, such as combretastatin A-4 phosphate disodium salt or combretastatin A-1 phosphate disodium salt, and the anticancer agent, such as cisplatin are formulated and administered separately.

FIG. 2: (A) Graph of therapeutic synergy observed with the combination of CA4P and the Peak Tumor Concentration Agent, cisplatin in the M5076DDP tumor model. Drug treatment was iv, Q4D×3. Drug combinations were administered simultaneously. (B) Graph showing CA4P significantly enhanced the antitumor activity of an otherwise inactive dose of cisplatin (3 mg/kg/inj).

FIG. 3: (A) Graph of therapeutic synergy observed with the combination of CA4P and the peak tumor concentration agent, carboplatin in the M5076 murine fibrosarcoma model. Drug treatment was intraperitoneal (ip), Q4D×3. Drug combinations were administered simultaneously ip (admixed). (B) Graph showing that CA4P, at three different dose levels (90–250 mg/kg/inj), significantly improved the antitumor activity of carboplatin.

Figure 4:
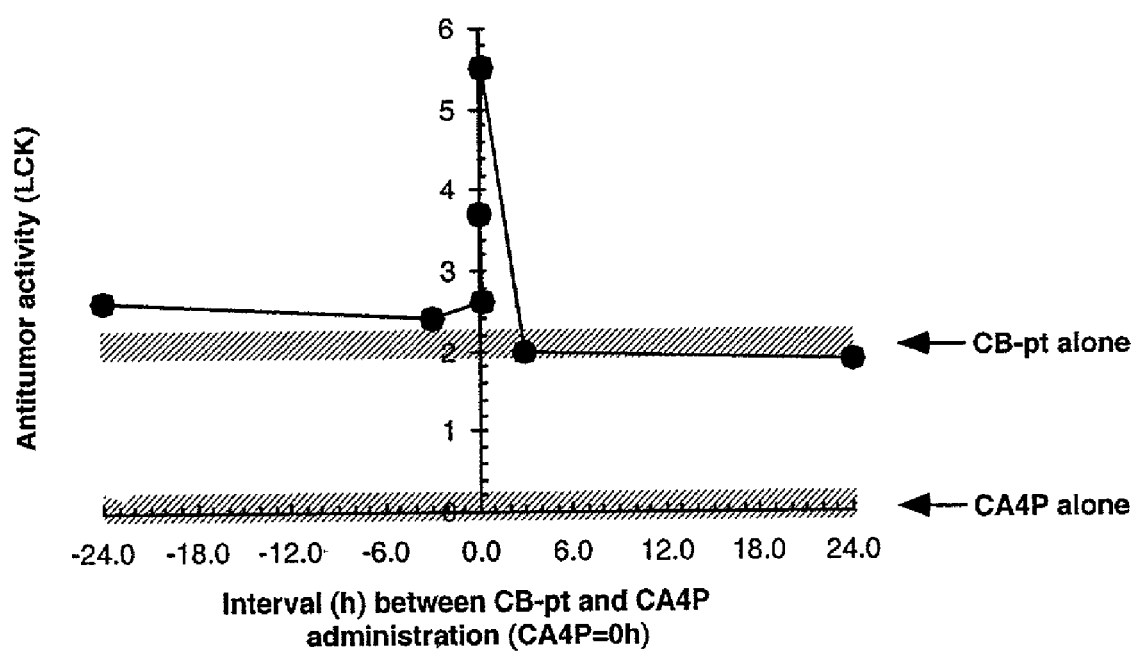

FIG. 4: A graph showing antitumor activity in log cell kill indicating that the CA4P and carboplatin should essentially be administered simultaneously.

Figure 5:
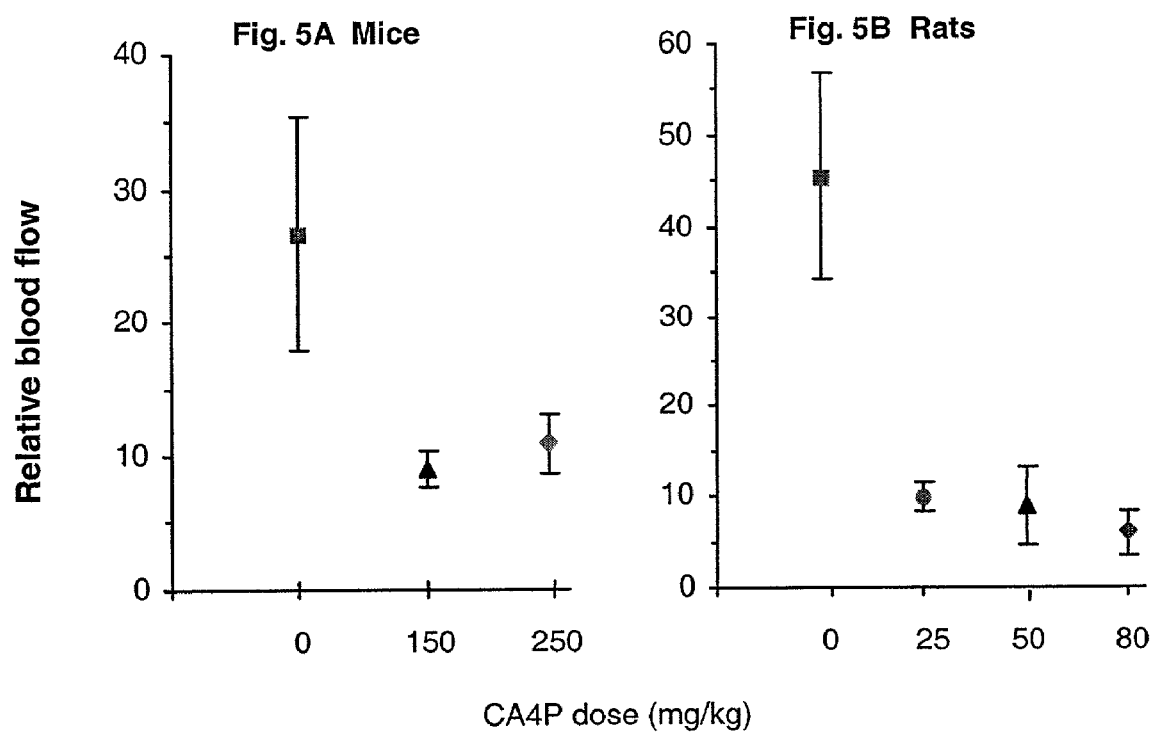

FIG. 5: Graph of inhibition of tumor blood flow by CA4P in the sc A2780 human ovarian carcinoma grown in nude mice (A) or nude rats (B).

Figure 6:
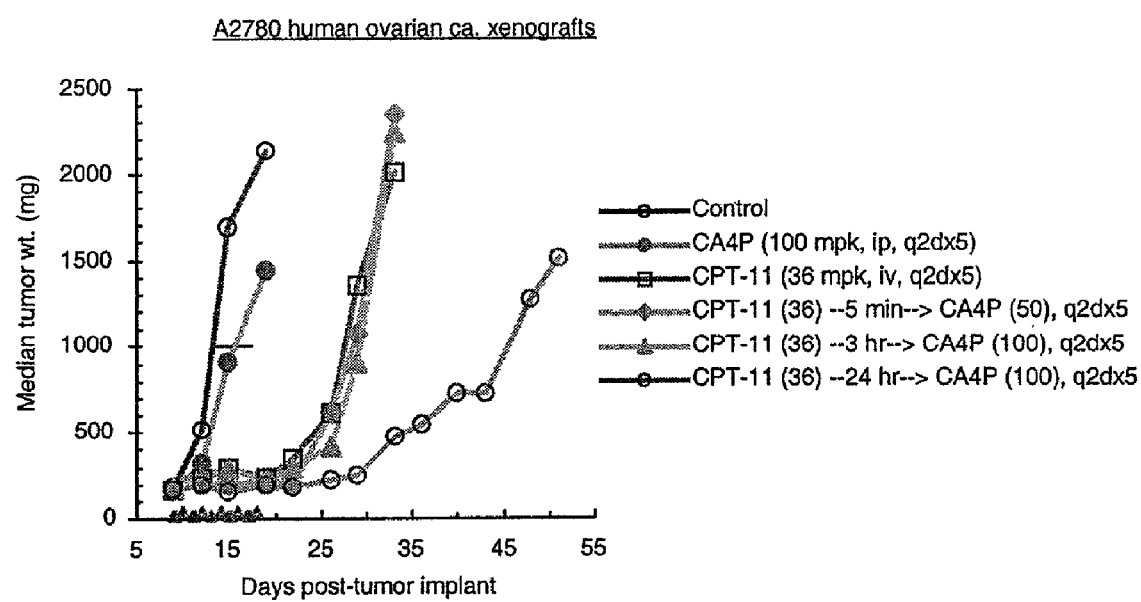

FIG. 6: Graph showing the antitumor effects of combined High AUC Agent, CPT-11, and CA4P chemotherapy in human ovarian carcinoma cells (A2780). CPT-11 is administered 3–24 hours prior to the administration of the combretastatin compound.

Figure 7A:
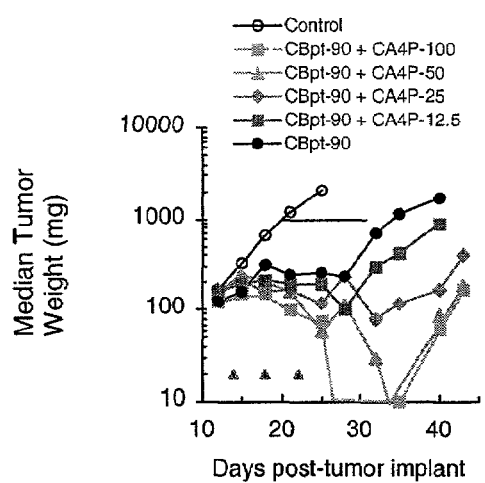
Figure 7B:
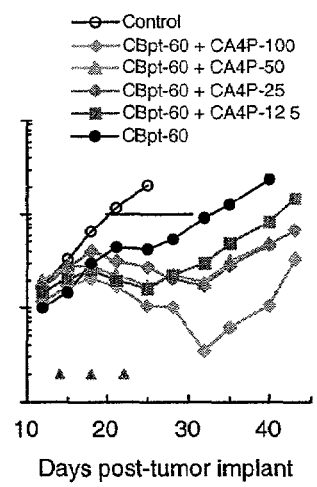
Figure 7C:
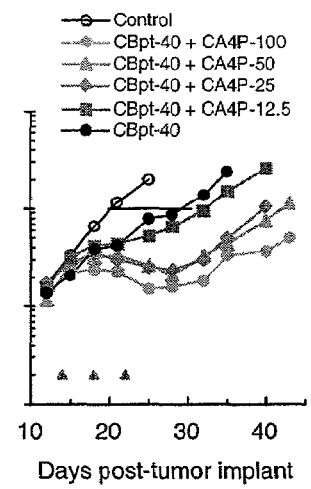

FIG. 7: Enhancement of the antitumor efficacy of carboplatin by low dose CA4P in the M5076/DDP tumors. Panels A-C depict results for the combination of various doses of CA4P with 90, 60 and 40 mg/m$^2$ of carboplatin, respectively.

Figure 8:
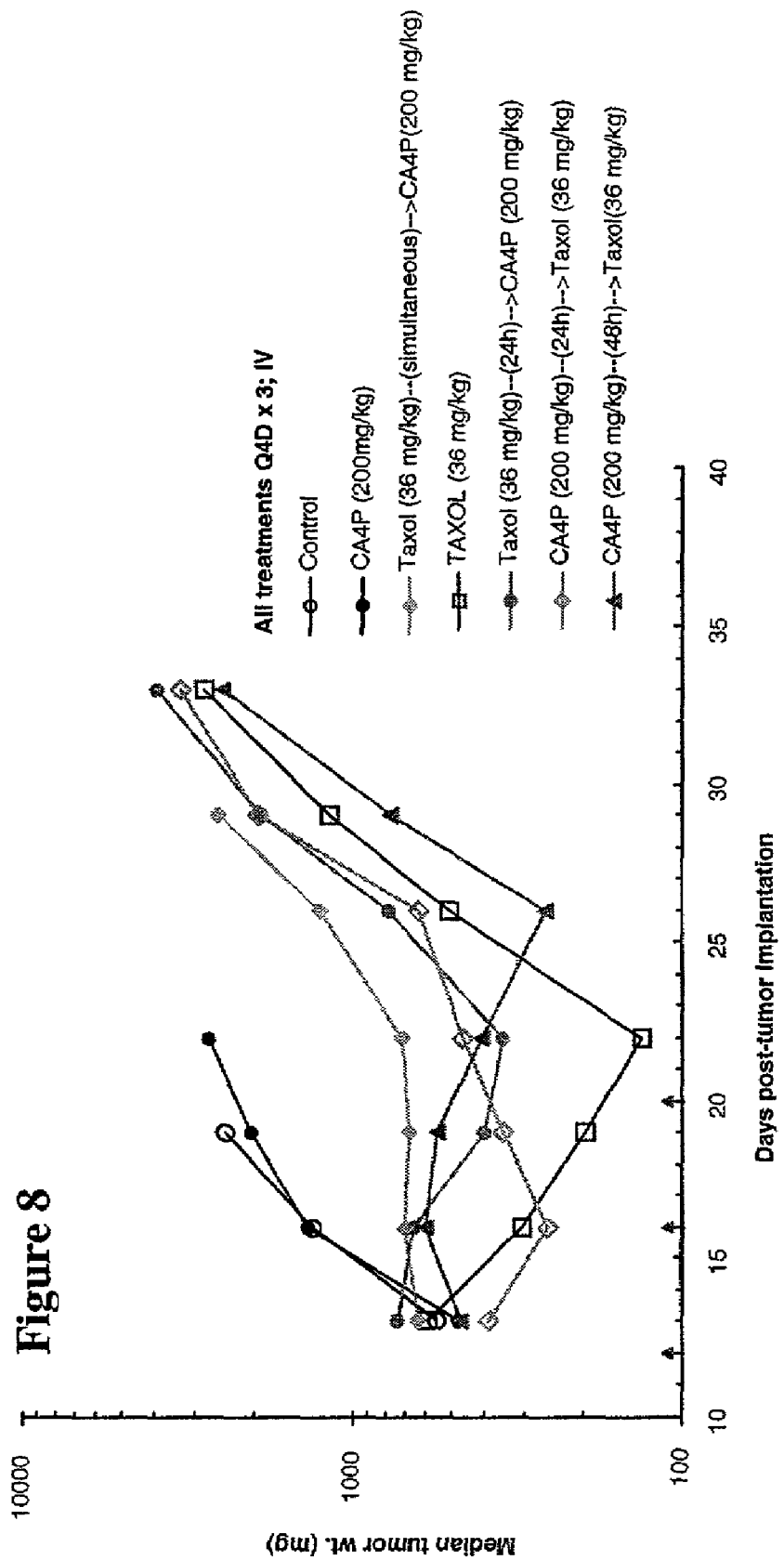

FIG. 8: Combination chemotherapy with CA4P and paclitaxel versus the 16/c murine mammary carcinoma.

Figure 9:
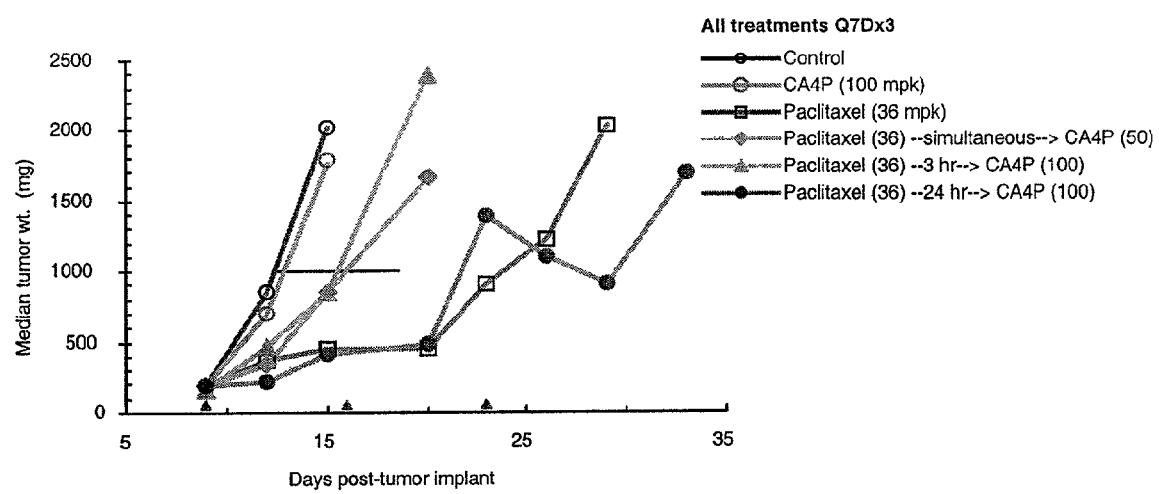

FIG. 9: Combination chemotherapy with CA4P and paclitaxel versus A2780 human ovarian carcinoma. Simultaneous administration of the agents is antagonistic in this model.

Figure 10:
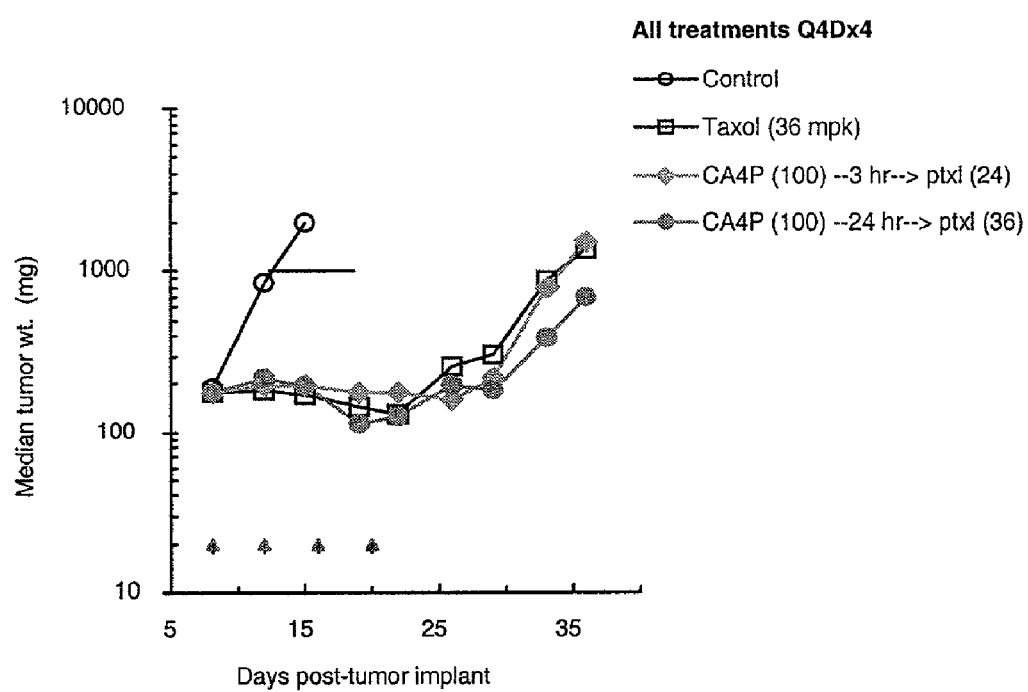

FIG. 10: Combination chemotherapy with CA4P and paclitaxel versus A2780 human ovarian carcinoma. An interval of 3 hours between treatments abrogates negative interaction.

Figure 11:
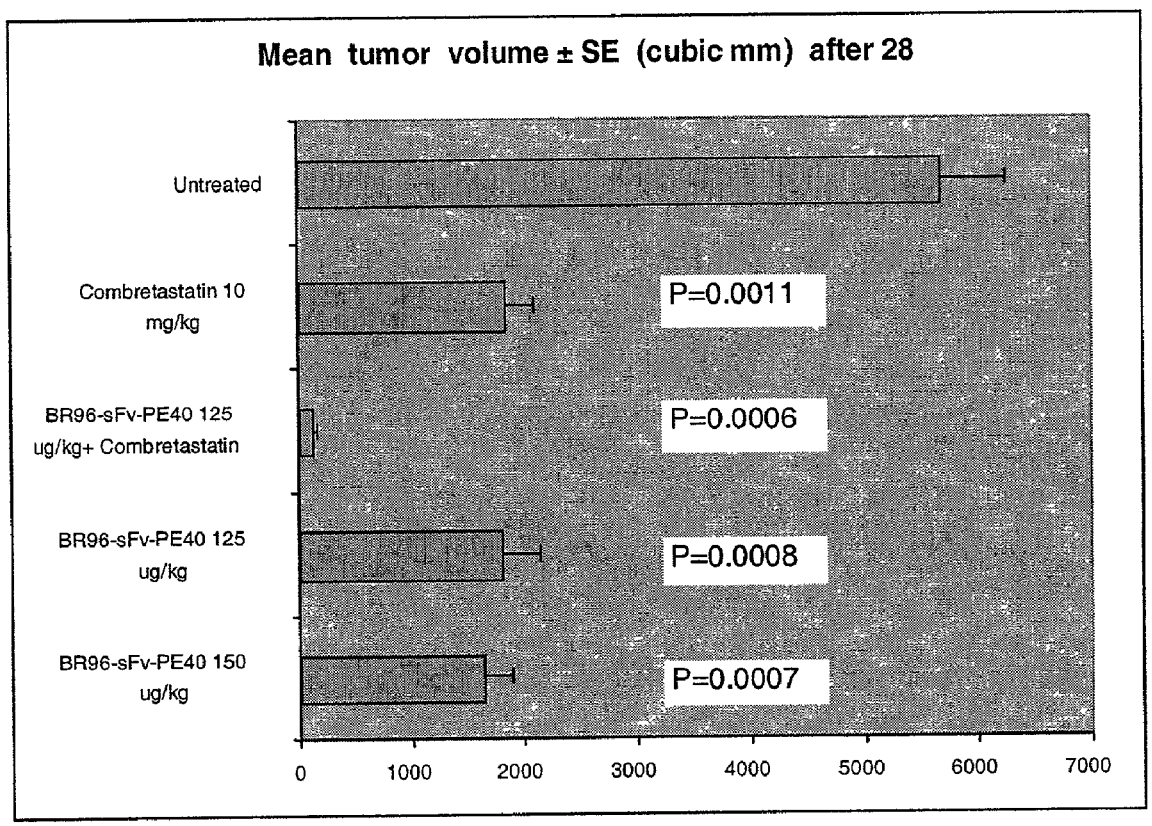

FIG. 11: A bar graph showing that combined administration of an immunotoxin BR96-sFv-PE40 with combretastatin A4P acts synergistically to reduce tumor size in a colon cancer xenograft model in an allogeneic Brown-Norway rat host.

Figures 12A, 12B:
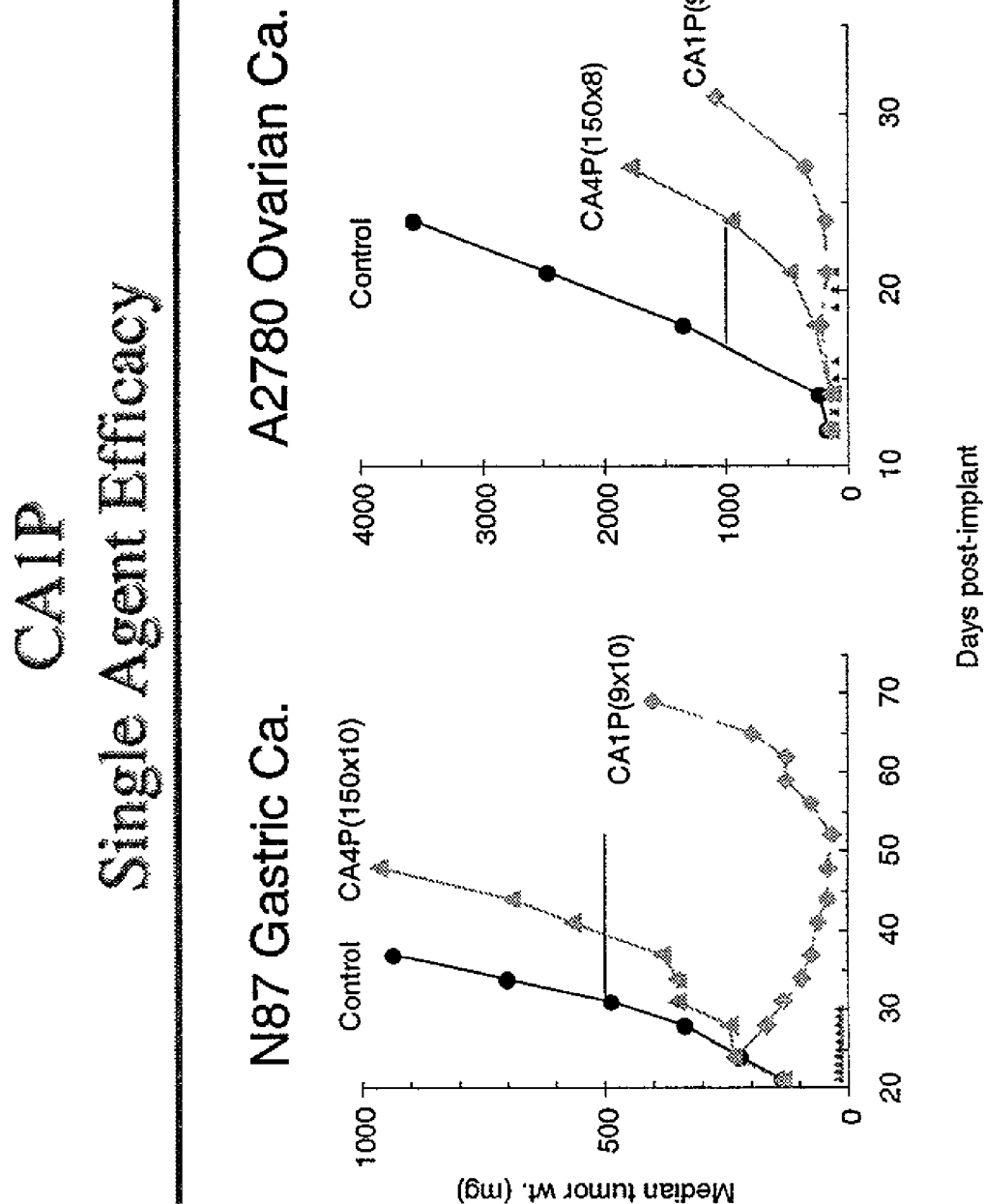

FIGS. 12A and 12B: A pair of graphs showing that combretastatin A-1P inhibits blood flow in human tumor xenografts in nude mice in a manner comparable to that observed for combretastatin A-4P. FIG. 12A: N87 gastric cancer xenograft model; FIG. 12B: A2780 ovarian cancer xenograft model.

FIGS. 13A–13D are a series of graphs showing dose response curves of tumor size reduction in response to administration of combretastatin A-1P and carboplatin alone and in combination against an M5076 fibrosarcoma xenograft model. Combined administration of combretastatin A-1P and carboplatin acted synergistically to reduce tumor size.

Figure 14:
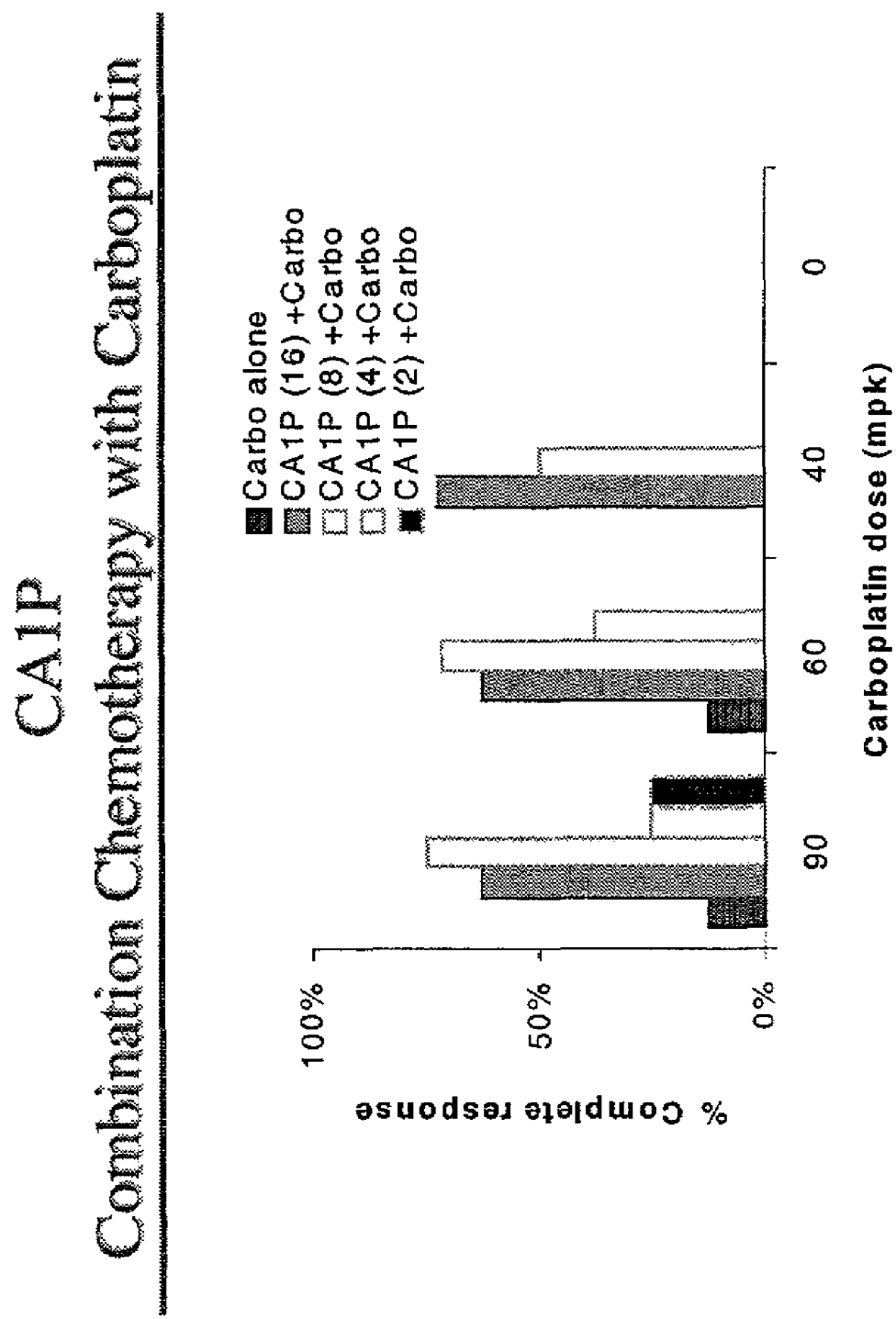

FIG. 14: Graph showing that combined administration of combretastatin A-1P and carboplatin produces a synergistic antitumor effect, producing a complete response (disappearance of tumors) not observed in single agent therapy.

Figure 15:
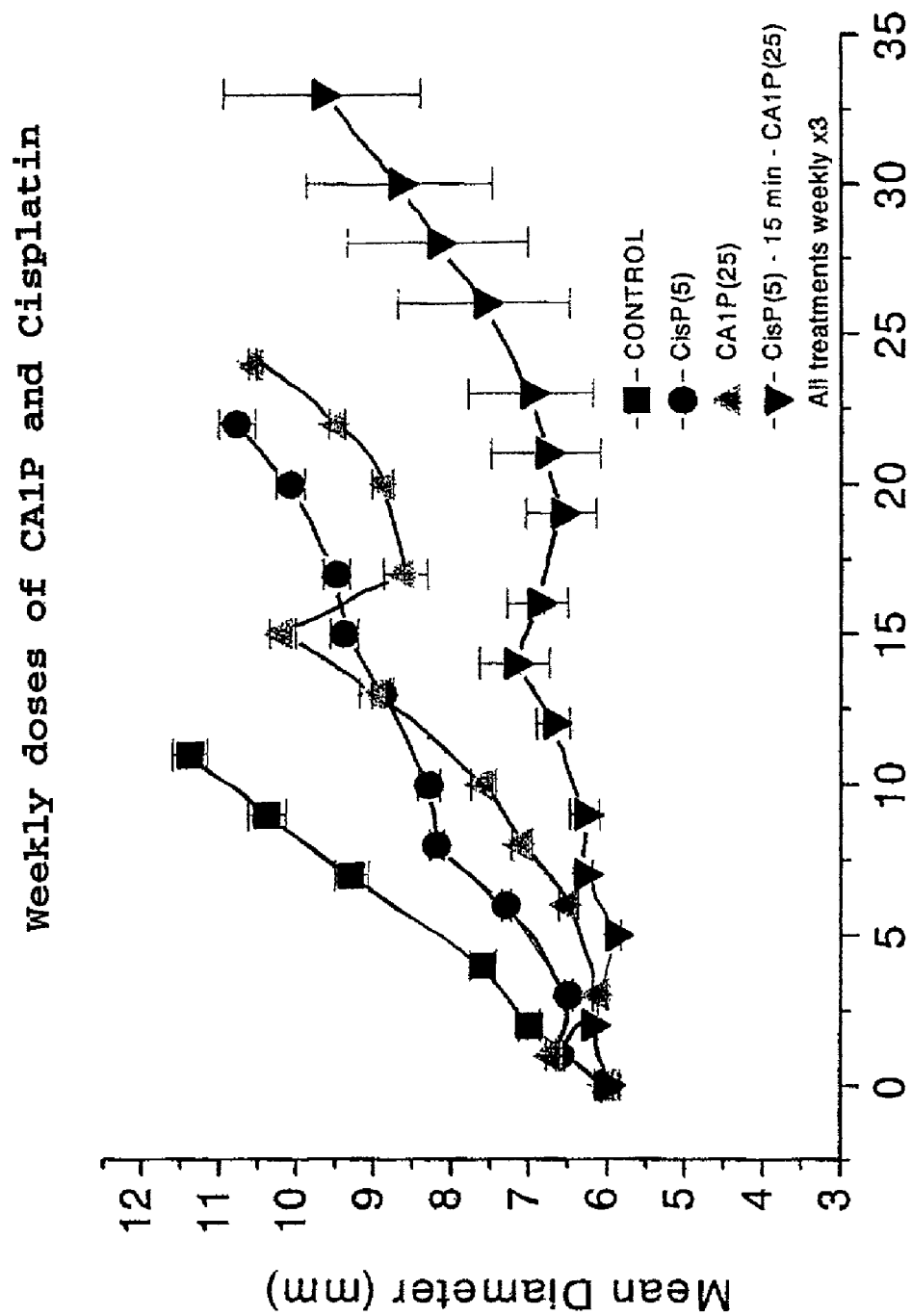

FIG. 15: A graph showing that combined administration of cisplatin and combretastatin A1P act synergistically to reduce tumor size in a CaNT breast tumor model in CBA mice.

DETAILED DESCRIPTION OF THE INVENTION

In accordance with the present invention, improved chemotherapeutic regimens are provided for the treatment of cancer. The improved chemotherapeutic regimens can lower side effects and enhance efficacy for the treatment of neoplastic disease.

Derived from the South African tree Combretum caffrum, combretastatin A-4 (CA-4) was initially identified in the 1980's as a potent inhibitor of tubulin polymerization. CA-4 binds a site at or near the colchicine binding site on tubulin with high affinity. In vitro studies clearly demonstrated that CA-4 is a potent cytotoxic agent against a diverse spectrum of tumor cell types in culture. Combretastatin A-4 has also recently been shown to have an additional "antivascular" mechanism of action. A number of studies have shown that CA4P causes extensive shut-down of blood flow to the tumor vasculature, leading to secondary tumor cell death. Blood flow to normal tissues is generally far less affected by combretastatin A-4 than tumors, although blood flow to some organs, such as spleen, skin, skeletal muscle and brain, can be inhibited. In light of this new "non-cytotoxic" mode of action of CA4P, there is considerable interest in exploiting the novel anti-vascular action of CA4P for cancer treatment. Recently, single agent efficacy was reported for CA4P using a frequent dosing regimen. Another report suggested that large tumors can, in some cases, be more responsive to CA4P therapy than small tumors.

Combretastatin A-1 and prodrugs thereof (CA1P) are also potent inhibitors of tubulin polymerization. CA1P has also been shown to cause shut down of blood flow to the tumor vasculature.

Pharmaceutical Compositions

As explained above, the present methods can, for example, be carried out using a single pharmaceutical composition comprising both combretastatin A-4 compound or combretastatin A-1 compound and anticancer agent(s) (when administration is to be simultaneous) or using two or more pharmaceutical compositions separately comprising combretastatin A-4 compound or combretastatin A-1 compound and anticancer agent(s) (when administration is to be simultaneous or sequential). Such pharmaceutical compositions can comprise, inter alia, at least one anticancer agent and/or a combretastatin A-4 compound or combretastatin A-1 compound, such as combretastatin A-4 phosphate disodium salt or combretastatin A-1 phosphate disodium salt and a pharmaceutically acceptable carrier. The phrase "pharmaceutically acceptable" refers to molecular entities and compositions that are physiologically tolerable and preferably do not produce an allergic or similar untoward reaction, such as gastric upset, dizziness and the like, when administered to a human.

Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers, for example to a diluent, adjuvant, excipient, auxiliary agent or vehicle with which an active agent of the present invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

A pharmaceutical composition of the present invention can be administered by any suitable route, for example, by injection, by oral, pulmonary, nasal or other forms of administration. In general, pharmaceutical compositions contemplated to be within the scope of the invention, comprise, inter alia, pharmaceutically acceptable diluents, preservatives, solubilizers, emulsifiers, adjuvants and/or carriers. Such compositions can include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington's Pharmaceutical Sciences, 18th Ed. (1990, Mack Publishing Co., Easton, Pa. 18042) pages 1435–1712 which are herein incorporated by reference. A pharmaceutical composition of the present invention can be prepared, for example, in liquid form, or can be in dried powder, such as lyophilized form. Particular methods of administering such compositions are described infra.

Methods for Modulating Tumor Growth or Metastasis

As explained above, the present invention is directed towards methods for modulating tumor growth and metastasis comprising, inter alia, the administration of a combretastatin A-4 compound or combretastatin A-1 compound, such as combretastatin A-4 phosphate disodium salt or combretastatin A-1 phosphate disodium salt, and at least one anticancer agent. The agents of the invention can be administered separately (e.g., formulated and administered separately), or in combination as a pharmaceutical composition of the present invention. Administration can be achieved by any suitable route, such as parenterally, transmucosally, e.g., orally, nasally, or rectally, or transdermally. Preferably, administration is parenteral, e.g., via intravenous injection. Alternative means of administration also include, but are not limited to, intra-arteriole, intramuscular, intradermal, subcutaneous, intraperitoneal, intraventricular, and intracranial administration, or by injection into the tumor(s) being treated or into tissues surrounding the tumor(s).

The combretastatin A-4 compound or combretastatin A-1 compound, such as combretastatin A-4 phosphate disodium salt or combretastatin A-1 phosphate disodium salt and anticancer agent may be employed in any suitable pharmaceutical formulation, as described above, including in a vesicle, such as a liposome [see Langer, Science 249: 1527–1533 (1990); Treat et al., in Liposomes in the Therapy of Infectious Disease and Cancer, Lopez-Berestein and Fidler (eds.), Liss: New York, pp. 317–327, see generally, ibid] Preferably, administration of liposomes containing the agents of the invention is parenteral, e.g., via intravenous injection, but also may include, without limitation, intra-arteriole, intramuscular, intradermal, subcutaneous, intraperitoneal, intraventricular, and intracranial administration, or by injection into the tumor(s) being treated or into tissues surrounding the tumor(s).

In yet another embodiment, a pharmaceutical composition of the present invention can be delivered in a controlled release system, such as using an intravenous infusion, an implantable osmotic pump, a transdermal patch, liposomes, or other modes of administration. In a particular embodiment, a pump may be used [see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)]. In another embodiment, polymeric materials can be used [see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)]. In yet another embodiment, a controlled release system can be placed in proximity of the target tissues of the animal, thus requiring only a fraction of the systemic dose [see, e.g., Goodson, in Medical Applications of Controlled Release, supra, vol. 2, pp. 115–138 (1984)]. In particular, a controlled release device can be introduced into an animal in proximity of the site of inappropriate immune activation or a tumor. Other controlled release systems are discussed in the review by Langer [Science 249:1527–1533 (1990)]. The following Table I sets forth preferred chemotherapeutic combinations and exemplary dosages for use in the methods of the present invention. Where "Combretastatin A-4" appears, combretastatin A-4, combretastatin A-1 or a phosphate prodrug salt of either combretastatin A-4 or combretastatin A-1 or, such as CA4P or CA1P, is preferably employed.

| CHEMOTHERAPEUTIC COMBINATION | DOSAGE $mg/m^2$ (per dose) |
|---|---|
| Combretastatin A-4 | 1–100 mg/m2 |
| + Cisplatin | 5–150 mg/m2 |
| Combretastatin A-4 | 1–100 mg/m2 |
| + Carboplatin | 5–1000 mg/m2 |
| Combretastatin A-4 | 1–100 mg/m2 |
| + Radiation | 200–8000 cGy |
| Combretastatin A-4 | 1–100 mg/m2 |
| + CPT-11 | 5–400 mg/m2 |
| Combretastatin A-4 | 1–100 mg/m2 |
| + Paclitaxel | 40–250 mg/m2 |
| Combretastatin A-4 | 1–100 mg/m2 |
| + Paclitaxel | 40–250 mg/m2 |
| + Carboplatin | 5–1000 mg/m2 |
| Combretastatin A-4 | 1–100 mg/m2 |
| + 5FU and optionally | 5–5000 mg/m2 |
| + Leucovorin | 5–1000 mg/m2 |
| Combretastatin A-4 | 1–100 mg/m2 |
| + Epothilone | 1–500 mg/m2 |
| Combretastatin A-4 | 1–100 mg/m2 |
| + Gemcitabine | 100–3000 mg/m2 |
| Combretastatin A-4 | 1–100 mg/m2 |
| + UFT and optionally | 50–800 mg/m2 |
| + leucovorin | 5–1000 mg/m2 |
| Combretastatin A-4 | 1–100 mg/m2 |
| + Gemcitabine | 100–3000 mg/m2 |
| + Cisplatin | 5–150 mg/m2 |
| Combretastatin A-4 | 1–100 mg/m2 |
| + UFT | 50–800 mg/m2 |
| + Leucovorin | 5–1000 mg/m2 |
| Combretastatin A-4 | 1–100 mg/m2 |
| + Cisplatin | 5–150 mg/m2 |

-continued

| CHEMOTHERAPEUTIC COMBINATION | DOSAGE mg/m² (per dose) |
|---|---|
| + paclitaxel | 40–250 mg/m2 |
| Combretastatin A-4 | 1–100 mg/m2 |
| + Cisplatin | 5–150 mg/m2 |
| + 5FU | 5–5000 mg/m2 |
| Combretastatin A-4 | 1–100 mg/m2 |
| + Oxaliplatin | 5–200 mg/m2 |
| + CPT-11 | 4–400 mg/m2 |
| Combretastatin A-4 | 1–100 mg/m2 |
| + 5FU | 5–5000 mg/m2 |
| + CPT-11 and optionally | 4–400 mg/m2 |
| + leucovorin | 5–1000 mg/m2 |
| Combretastatin A-4 | 1–100 mg/m2 |
| + 5FU | 5–5000 mg/m2 |
| + radiation | 200–8000 cGy |
| Combretastatin A-4 | 1–100 mg/m2 |
| + radiation | 200–8000 cGy |
| + 5FU | 5–5000 mg/m2 |
| + Cisplatin | 5–150 mg/m2 |
| Combretastatin A-4 | 1–100 mg/m2 |
| + Oxaliplatin | 5–200 mg/m2 |
| + 5FU and optionally | 5–5000 mg/m2 |
| + Leucovorin | 5–1000 mg/m2 |
| Combretastatin A-4 | 1–100 mg/m2 |
| + paclitaxel | 40–250 mg/m2 |
| + CPT-11 | 4–400 mg/m2 |
| Combretastatin A-4 | 1–100 mg/m2 |
| + paclitaxel | 40–250 mg/m2 |
| + 5FU | 5–5000 mg/m2 |
| Combretastatin A-4 | 1–100 mg/m2 |
| + UFT | 50–800 mg/m2 |
| + CPT-11 and optionally | 4–400 mg/m2 |
| + leucovorin | 5–1000 mg/m2 |
| Combretastatin A-4 | 1–100 mg/m2 |
| + BR96-sFv-PE40 | 100–750 mg/m2 |

In the above Table I, "5FU" denotes 5-fluorouracil, "Leucovorin" can be employed as leucovorin calcium, "UFT" is a 1:4 molar ratio of tegafur: uracil, and "Epothilone" is preferably a compound described in WO 99/02514 or WO 00/50423, both incorporated by reference herein in their entirety.

While Table I provides exemplary dosage ranges of the combretastatin A-4 compounds or combretastatin A-1 compounds and certain anticancer agents of the invention, when formulating the pharmaceutical compositions of the invention the clinician may utilize preferred dosages as warranted by the condition of the patient being treated. For example, combretastatin A-4 compounds or combretastatin A-1 compounds may preferably be administered at a dosage ranging from 30–70 mg/m2 every three weeks for as long as treatment is required. Preferred dosages for cisplatin are 75–120 mg/m2 administered every three weeks. Preferred dosages for carboplatin are within the range of 200–600 mg/m2 or an AUC of 0.5–8 mg/ml×min; most preferred is an AUC of 4–6 mg/ml×min. When the method employed utilizes radiation, preferred dosages are within the range of 200–6000 cGY. Preferred dosages for CPT-11 are within 100–125 mg/m2, once a week. Preferred dosages for paclitaxel are 130–225 mg/m2 every 21 days. Preferred dosages for gemcitabine are within the range of 80–1500 mg/m2 administered weekly. Preferably UFT is used within a range of 300–400 mg/m2 per day when combined with leucovorin administration. Preferred dosages for leucovorin are 10–600 mg/m2 administered weekly. A preferred dose of the Br96-sFv-PE40 immunotoxin is 420 mg/m2. The use of the BR96-sFv-PE40 immunotoxin in combination with combretastatin A4 and its prodrugs in immune enhancing therapy is described in U.S. Provisional Application 60/258,283, filed Dec. 26, 2000, the entire disclosure of which is incorporated by reference herein.

Certain cancers can be treated effectively with combretastatin A-4 or combretastatin A-1 and a plurality of anticancer agents. Such triple and quadruple combinations can provide greater efficacy. When used in such triple and quadruple combinations the dosages set forth above can be utilized. Other such combinations in the above Table I can therefore include "combretastatin A-4 or combretastatin A-1" in combination with (1) mitoxantrone+prednisone; (2) doxorubicin+taxane; or (3) herceptin+taxane. 5-FU can be replaced by UFT in any of the above combinations.

When employing the methods or compositions of the present invention, other agents used in the modulation of tumor growth or metastasis in a clinical setting, such as antiemetics, can also be administered as desired.

The following examples are provided to illustrate embodiments of the invention. They are not intended to limit the invention in any way.

The following protocols are provided to facilitate the practice of Examples I and II.

Drug administration: For administration to rodents, CA4P was dissolved in normal saline (0.9% NaCl). Paclitaxel was dissolved in a 50/50 mixture of ethanol and Cremophor® and stored at 4° C.; final dilution of paclitaxel was obtained immediately before drug administration with NaCl 0.9%. Fresh preparation of paclitaxel was employed to avoid precipitation. CPT-11 was dissolved in normal saline.

The volume of all compounds injected was 0.01 ml/g of mice, and 0.005 ml/g of rats.

In Vivo Antitumor Testing: The following tumor models were used: A2780 human ovarian carcinoma, the murine fibrosarcoma M5076 and M5076/ddp (resistant to cisplatin and carboplatin).

The human tumors were maintained in Balb/c nu/nu nude mice. M5076 and M5076ddp was maintained in C57BL/6 mice. Tumors were propagated as subcutaneous transplants in the appropriate mouse strain using tumor fragments obtained from donor mice.

The following tumors were passaged in the indicated host strain of mouse: murine M5076 fibrosarcoma (M5076) in C57Bl/6 mice; human A2780 ovarian carcinomas in nude mice. Tumor passage occurred biweekly for murine tumors and approximately every two to three weeks for the human tumor line. With regard to efficacy testing, M5076 and M5076 ddp tumors were implanted in (C57Bl/6×DBA/2)F1 hybrid mice, and human tumors were implanted in nude mice. All tumor implants for efficacy testing were subcutaneous (sc).

The required number of animals needed to detect a meaningful response were pooled at the start of the experiment and each was given a subcutaneous implant of a tumor fragment (≈50 mg) with a 13-gauge trocar. For treatment of early-stage tumors, the animals were again pooled before distribution to the various treatment and control groups. For treatment of animals with advanced-stage disease, tumors were allowed to grow to the pre-determined size window (tumors outside the range were excluded) and animals were evenly distributed to various treatment and control groups. Treatment of each animal was based on individual body weight. Treated animals were checked daily for treatment related toxicity/mortality. Each group of animals was weighed before the initiation of treatment (Wt1) and then again following the last treatment dose (Wt2). The difference in body weight (Wt2−Wt1) provides a measure of treatment-related toxicity.

Tumor response was determined by measurement of tumors with a caliper twice a week, until the tumors reach a predetermined "target" size of 1 gm. Tumor weights (mg) were estimated from the formula:

Tumor weight=(length×width2)÷2

Antitumor activity was evaluated at the maximum tolerated dose (MTD) which is defined as the dose level immediately below which excessive toxicity (i.e. more than one death) occurred. The MTD was frequently equivalent to OD. When death occurs, the day of death was recorded. Treated mice dying prior to having their tumors reach target size were considered to have died from drug toxicity. No control mice died bearing tumors less than target size. Treatment groups with more than one death caused by drug toxicity were considered to have had excessively toxic treatments and their data were not included in the evaluation of a compound's antitumor efficacy.

Tumor response end-point was expressed in terms of tumor growth delay (T-C value), defined as the difference in time (days) required for the treated tumors (T) to reach a predetermined target size compared to those of the control group (C).

To estimate tumor cell kill, the tumor volume doubling time was first calculated with the formula:

TVDT=Median time (days) for control tumors to reach target size−Median time (days) for control tumors to reach half the target size and, Log cell kill=$T$-$C$÷(3.32×$TVDT$)

Statistical evaluations of data were performed using Gehan's generalized Wilcoxon test.

EXAMPLE I

Combretastatin A-4 phosphate disodium salt, an agent with a dual mechanism of action, was evaluated for in vivo antitumor activity with the Peak Concentration Agents, cisplatin and carboplatin. When administered daily as a single agent for ten days to tumor bearing mice, combretastatin A-4 phosphate disodium salt demonstrated significant antitumor activity against the cisplatin-resistant M5076DDP murine fibrosarcoma, producing 1.1 log cell kill. See FIG. 1.

In a combination chemotherapy trial, therapeutic synergy was observed with both cisplatin and carboplatin. In tumor perfusion studies, combretastatin A-4 phosphate disodium salt significantly inhibited tumor blood flow in the A2780 human ovarian tumor xenografts in mice (67% inhibition) and in rats (87% inhibition).

In order to better assess the therapeutic potential of combretastatin A-4 phosphate disodium salt, studies were conducted to evaluate three aspects of CA4P's pharmacology: [1] antitumor efficacy as a single agent, [2] antitumor efficacy in combination with cisplatin, carboplatin, paclitaxel, or CPT-11 and [3] effects on tumor blood flow.

Results

Figure 1:
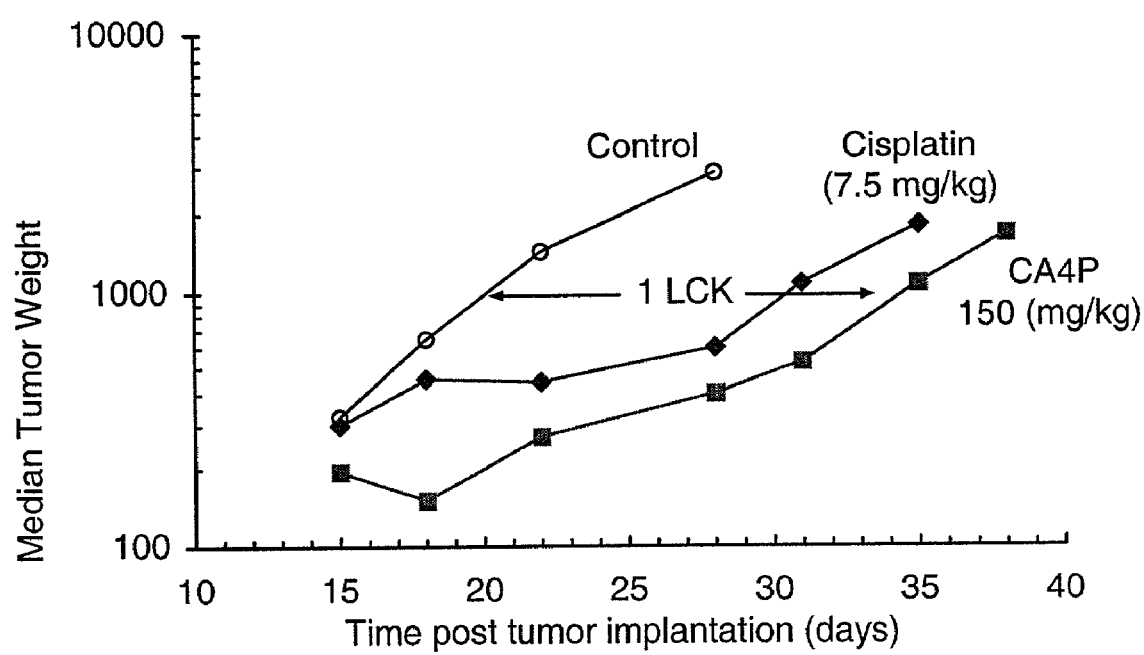
FIG. 1: Graph of the antitumor activity of cisplatin and combretastain A-4 phosphate disodium salt (CA4P) administered singly in the moderately platinum-resistant M5076DDP murine fibrosarcoma. Tumor was staged to 300 mg at treatment initiation. Cisplatin was administered intravenously (iv) every 4 days for 3 doses (Q4D×3). CA4P was given iv, every day for 10 days (Monday through Friday).

Single Agent Efficacy Against the Cisplatin-Resistant sc M5076DDP Tumor Model M5076DDP is a murine fibrosarcoma that has developed resistance to cisplatin and cross-resistance to carboplatin. Combretastatin A-4 phosphate disodium salt treatment of mice bearing staged M5076DDP tumors using an everyday× 10 (Monday thru Friday) schedule produced moderate but significant antitumor effects. At its optimal dose (150 mg/kg/inj), combretastatin A-4 phosphate disodium salt yielded 1.1 log cell kill (LCK). In comparison, single agent cisplatin administered at its optimal schedule (every four days for three doses; Q4D×3) yielded 0.8 LCK at its MTD of 7.5 mg/kg/inj (FIG. 1).

Combination Chemotherapy with Platinum Drugs

Figure 2B:
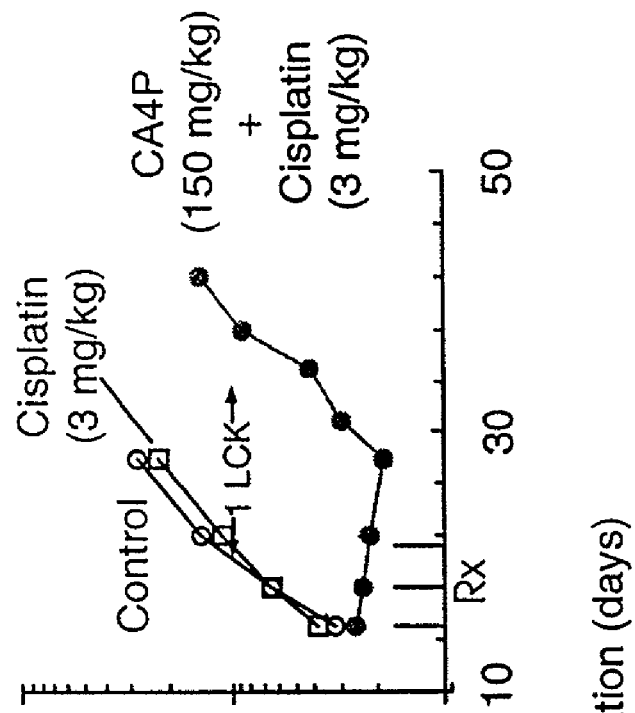
Figure 2A:
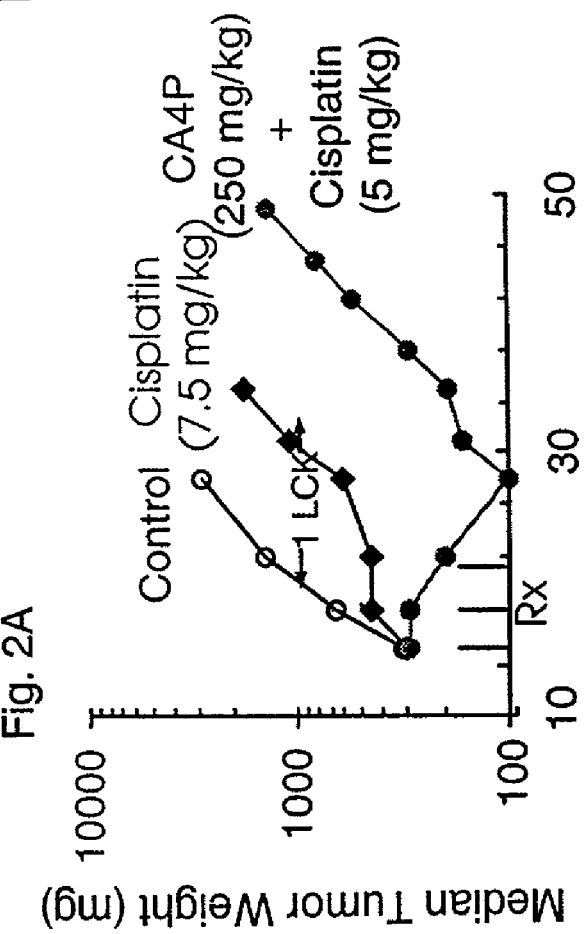

Therapeutic synergy was achieved when combretastatin A-4 phosphate disodium salt was combined with cisplatin (administered simultaneously) in the treatment of advanced staged (300 mg) sc M5076DDP tumors. Single agent cisplatin produced 0.8 LCK at its maximum tolerated dose (MTD) of 7.5 mg/kg/inj, q4d×3. In comparison, the maximally tolerated combination of combretastatin A-4 phosphate disodium salt (250 mg/kg/inj)+Cisplatin (5 mg/kg/inj) yielded 2.0 LCK (FIG. 2A). It is of interest that the combination produced significant shrinkage of tumors following treatment, whereas single agent cisplatin did not (FIG. 1). Another noteworthy aspect of this synergistic combination regimen is the ability of combretastatin A-4 phosphate disodium salt to substantially improve the efficacy of an otherwise inactive (lower) dose of cisplatin (FIG. 2B).

Combination with Carboplatin (CPt) Versus sc M5076

Combretastatin A-4 phosphate disodium salt also produced synergistic antitumor activity when used in combination with carboplatin against large sc M5076 tumors (H300 mg). In this sensitive tumor model, carboplatin produced 1.4 LCK, but with no tumor regression, at its MTD of 90 mg/kg/inj, iv, q4d×3. In comparison the best combination yielded 2.0 LCK which was accompanied by significant tumor shrinkage (FIG. 3A). Two important aspects of the tumor response elicited by the combretastatin A-4 phosphate disodium salt+carboplatin combination regimen are [1] the optimal combretastatin A-4 phosphate disodium salt dose required for therapeutic synergy (<90 mg/kg/inj) was significantly lower than its MTD as a single agent (>250 mg/kg/inj) (FIG. 3B); [2] the carboplatin dose (90 mg/kg/inj when administered as single agent) required to produce optimal antitumor effects, is greatly reduced when used in combination with combretastatin A-4 phosphate disodium salt (FIG. 3B).

Timing Studies (Carboplatin+CA4P)

The data presented in FIG. 4 indicate that Carboplatin ("CB-pt") and CA4P are preferably administered more or less simultaneously. Most preferably carboplatin is administered immediately before CA4P. The tumor model shown in this graph is M5076 ddp (a platinum resistant variant of M5076 murine fibrosarcoma).

Effects of CA4P on Tumor Perfusion

The effects of combretastatin A-4 phosphate disodium salt on tumor perfusion were studied using the Evans blue dye uptake assay. Mice or rats bearing sc A2780 human ovarian carcinoma were administered an iv dose of combretastatin A-4 phosphate disodium salt. An hour later, Evans blue was injected iv. The amount of Evans blue accumulated in the tumor is proportional to the blood flow through the tumor. Using this technique, it was shown that CA4P dramatically inhibited blood flow to the tumors, both in mice and rats, causing at optimal dose a 67% and 87% reduction of tumor blood flow, respectively (FIGS. 5A and 5B).

Combination Chemotherapy with CPT-11

A combination chemotherapy study was conducted to evaluate the antitumor activity of combined CPT-11 and combretastatin A-4 phosphate disodium salt treatment. Various dosing schedules were used in accordance with the invention ranging from administering the two agents virtually simultaneously (5 min apart) to CPT-1 preceding CA4P by 3 or 24 hrs. At its MTD, CPT-11 produced 3.3 LCK. Administering the two agents simultaneously or 3 hr apart gave equivalent results to CPT-11 alone. However, when CPT-11 preceded CA4P by 24 hr, an enhanced antitumor effect was observed (FIG. 6) demonstrating a preferred embodiment of the invention.

Minimum Efficacious Dose-Pharmacokinetics Determination in Combination with Carboplatin Combretastatin A-4 has demonstrated robust therapeutic synergism with cisplatin and carboplatin as shown herein. The doses of combretastatin A-4 phosphate disodium salt (CA4P) used in these previous combination studies has in general been between 100–250 mg/kg (200–750 mg/m2). Current human pharmacokinetics data indicate that preferred CA4P dosing is considerably lower (~50–60 mg/m2). A study was therefore conducted to determine the minimum CA4P dose needed for combination therapy with carboplatin in the modestly carboplatin resistant murine fibrosarcoma M5076/DDP. Using doses and treatment regimen (iv, q4d×3) of CA4P that have no single agent activity, it was demonstrated that CA4P at doses as low as 12.5–25 mg/m2 were sufficient to enhance the antitumor activity of carboplatin administered at a range of dose levels. See FIGS. 7A, 7B and 7C.

Determination of the Optimal Treatment Schedule for the Combination of Combretastain A-4 Phosphate Disodium Salt (CA4P) with Paclitaxel The present invention contemplates, for example, the administration of a combretastatin A-4 compound, such as CA4P with paclitaxel or with paclitaxel and carboplatin. A number of studies were conducted to determine an optimal treatment schedule, i.e, the sequence or the order, in which the two agents, CA4P and paclitaxel are administered. This consideration is deemed particularly important for this combination for two reasons: 1) CA4P is a tubulin depolymerizer while paclitaxel is a tubulin polymerizer, thus there may be potential for interaction at the tubulin level; and 2) CA4P inhibits tumor blood flow which may affect the regional micro-pharmacokinetics of paclitaxel in the tumors as well as the tumoral proliferative state. In an initial study in the 16/c mammary carcinoma model, there was a suggestion that administering the two agents simultaneously might adversely affect the overall efficacy of the combination (FIG. 8) in this model, while allowing an interval between drug administration restored the efficacy of the combination. Subsequently two other studies were conducted in the human ovarian carcinoma model A2780 to further define an optimal sequence and interval between drug administrations.

An initial study was conducted to assess the effects of administering paclitaxel simultaneously with CA4P or prior to CA4P. Results indicate that administration of the two agents simultaneously was deleterious to the overall efficacy of the combination in this model (FIG. 9). Allowing an interval of 3 hr between the administration of the two agents did not restore the overall efficacy of the combination, but overall efficacy was restored at an interval of 24 hours.

An additional study was conducted to evaluate the effects of administering CA4P prior to paclitaxel. The results demonstrated that allowing an interval of 3 hr between treatments with the two agents was sufficient to avoid negative interaction (FIG. 10).

Combination Chemotherapy with Immunotoxin

Studies assessing the efficacy of combined administration of CA4P with the immunotoxin BR96-sFv-PE40 were also conducted. The construction of the immunotoxin is described in Siegall et al. (1994) J. of Immunology 152: 2377–2384.

Five groups of 5 rats each were inoculated intrahepatically with $1.5\times10^5$ wild type colon cancer cells (BN7005-H1D2) on day 0. BR96-sFv-PE40 is an immunoconjugate of BR96 monoclonal antibody and Pseudomonas toxin PE40. BR96 recognizes Lewis y antigen on the colon carcinoma BN7005 rat tumor. The immunotoxin was inoculated at 2 different dose levels as indicated (125 μg/kg or 150 μg/kg respectively), on days 9, 12, 14, 16, 19, 21 and 23. Combretastatin A4 phosphate prodrug was administered ip 4–6 hours prior to the administration of the immunotoxin when administered on the same day as the immunotoxin on days 7, 8, 9, 12, 13, 14, 14, 16, 19 and 20. All rats were lapartomized on day 28 and liver tumor sizes measured by a caliper and tumor volume calculated.

As shown in FIG. 11, there was a significant different between the treatment group and the untreated controls. The results of the Student's t test are also shown in the figure. The differences between the combined treatment and CA4P or immunotoxin alone were also significant, p=0.002 and p=0.006, respectively. When treatment was stopped on day 28, the tumor subsequently grew rapidly in all groups. These data demonstrate the efficacy of CA4P and immunotoxin when administered in combination.

EXAMPLE II

Combination Chemotherapy with Combretastatin A-1P

Combretastatin A-1 phosphate disodium salt, an agent with a dual mechanism of action, was evaluated for in vivo antitumor activity with the Peak Concentration Agents, carboplatin, and cisplatin. When administered daily as a single agent for ten days to tumor bearing mice, combretastatin A-1 phosphate disodium salt demonstrated modest antitumor activity against the cisplatin-resistant M5076DDP murine fibrosarcoma.

In a combination chemotherapy trial, therapeutic synergy was observed with both cisplatin and carboplatin. In tumor perfusion studies, combretastatin A-1 phosphate disodium salt significantly inhibited tumor blood flow in both A2780 human ovarian tumor xenografts in mice and N87 gastric cancer tumor xenografts.

In order to better assess the therapeutic potential of combretastatin A-1 phosphate disodium salt, studies were conducted to evaluate three aspects of CA4P's pharmacology: [1] antitumor efficacy as a single agent, [2] antitumor efficacy in combination with cisplatin and carboplatin, and [3] effects on tumor blood flow.

Results

Single Agent Efficacy Against N87 Gastric Cancer
and A2780 Ovarian Cancer Xenografts CA1P demonstrated equivalent blood flow inhibition to that observed with CA4P in human tumor xenografts in nude mice but was 5–10 times more potent. Additionally, CA1P has demonstrated improved single agent activity in human tumor xenograft models, including N87 human gastric carcinoma, and the A2780 ovarian carcinoma. In A2780, CA1P achieved 2.1 LCK at its MTD of 9 mg/kg, ip, q1d×8, compared to 1.1 LCK for CA4P at 150 mg/kg, ip. See FIG. 12.

Combination Chemotherapy with Carboplatin and
Cisplatin

As shown in FIG. 13, combination chemotherapy demonstrated that CA1P enhanced the antitumor activity of carboplatin in a manner similar to what had been observed for CA4P. Synergistic antitumor activity was also demonstrated. Advantageously, the minimum effective dose required for synergistic enhancement was considerably lower for CA1P (4–8 mg/kg) as compared to CA4P (25–50 mg/kg). Additionally, when CA1P is administered in combination with carboplatin, synergistic antitumor activity producing complete response (disappearance of tumors) was observed. When either agent was administered alone, this response was not observed. See FIG. 14.

In additional studies, CA1P was administered in combination with cisplatin in a CaNT breasts tumor model I. As can be seen in FIG. 15, combined administration of cisplatin and CA1P acted synergistically to reduce tumor size.

CONCLUSION

The above described results readily demonstrate potentiation for a variety of combinations of anticancer agents with a combretastatin A-4 compound or combretastatin A-1 compound. Thus anticancer agents can be effectively used to modulate tumor growth or metastasis of tumors that previously had developed a resistance to such drugs. Additionally, the present inventors have developed methods for the treatment of cancer which permit the clinician to administer lowered dosages of anticancer agents with appropriate administration schedules thereby reducing unwanted side effects while maintaining efficacy.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims. For example, other combretastatins or even other antivascular agents can be employed in the present invention in place of the combretastatin A-4 compound or combretastatin A-1 compound.

What is claimed is:

1. A method for modulating tumor growth or metastasis in an animal in need thereof, comprising sequential or simultaneous administration of paclitaxel and combretastatin A-4 phosphate prodrug salt in amounts effective therefor.

2. A method for modulating tumor growth or metastasis in an animal in need thereof, comprising administration of combretastatin A-4 phosphate prodrug salt and paclitaxel, in amounts effective therefor, wherein said combretastatin A-4 phosphate prodrug salt is administered at a time relative to administration of said paclitaxel sufficient to modulate blood flow to said tumor to provide a time-dependent effective tumor concentration of said paclitaxel.

3. The method as claimed in claim 1 or 2, wherein said combretastatin A4 phosphate prodrug salt is administered at least 3 hours prior to paclitaxel.

4. A pharmaceutical composition for modulating tumor growth or metastasis in an animal in need thereof, comprising paclitaxel, and combretastatin A-4 phosphate prodrug salt, in amounts effective therefore in a pharmaceutically acceptable carrier.

* * * * *